United States Patent
Assaf et al.

(10) Patent No.: US 9,511,208 B2
(45) Date of Patent: Dec. 6, 2016

(54) SYSTEMS AND METHOD FOR BYPASSING AN ANASTOMOSIS SITE

(71) Applicant: Cologuard Ltd., Kfar-Saba (IL)

(72) Inventors: Boaz Assaf, Hod-HaSharon (IL); Eyal Teichman, Hod-HaSharon (IL)

(73) Assignee: Cologuard Ltd., Kfar-Saba (IL)

( * ) Notice: Subject to any disclaimer, the term of this patent is extended or adjusted under 35 U.S.C. 154(b) by 193 days.

(21) Appl. No.: 14/184,534

(22) Filed: Feb. 19, 2014

(65) Prior Publication Data
US 2014/0188029 A1 Jul. 3, 2014

Related U.S. Application Data

(63) Continuation of application No. 13/769,338, filed on Feb. 17, 2013, now Pat. No. 8,690,817, which is a (Continued)

(51) Int. Cl.
*A61M 5/00* (2006.01)
*A61M 27/00* (2006.01)
(Continued)

(52) U.S. Cl.
CPC ......... *A61M 27/002* (2013.01); *A61B 17/1114* (2013.01); *A61B 17/1155* (2013.01); *A61F 2/04* (2013.01); *A61B 2017/00473* (2013.01); *A61B 2017/00557* (2013.01); *A61B 2017/00867* (2013.01); *A61B 2017/1103* (2013.01); *A61B 2017/1132* (2013.01); *A61B 2017/1142* (2013.01); *A61B 2017/22054* (2013.01); *A61B 2017/306* (2013.01); *A61F 2002/045* (2013.01)

(58) Field of Classification Search
CPC .... A61F 2/04; A61F 2/0013; A61F 2002/045; A61F 2002/041; A61M 27/002; A61B 17/1114; A61B 17/1155
See application file for complete search history.

(56) References Cited

U.S. PATENT DOCUMENTS

| | | | |
|---|---|---|---|
| 3,435,820 | A | 4/1969 | Edwards |
| 3,435,823 | A | 4/1969 | Edwards |
| (Continued) | | | |

FOREIGN PATENT DOCUMENTS

| | | |
|---|---|---|
| CA | 2670302 | 1/2010 |
| CN | 101883539 | 11/2010 |
| (Continued) | | |

OTHER PUBLICATIONS

Notification of Office Action Dated Feb. 2, 2015 From The State Intellectual Property Office of the People's Republic of China Re. Application No. 201180060468.4 and Its Translation Into English.
(Continued)

*Primary Examiner* — Tatyana Zalukaeva
*Assistant Examiner* — Ariana Zimbouski

(57) ABSTRACT

A system for bypassing an anastomosis site in a hollow organ is provided. The system includes a sleeve configured for spanning the anastomosis site at an internal surface of the hollow organ and a band configured for attachment to an external surface of the hollow organ and limiting migration of the sleeve beyond the anastomosis site.

24 Claims, 20 Drawing Sheets

Related U.S. Application Data continuation-in-part of application No. PCT/IL2011/000934, filed on Dec. 8, 2011.

(60) Provisional application No. 61/524,343, filed on Aug. 17, 2011, provisional application No. 61/423,529, filed on Dec. 15, 2010.

(51) Int. Cl.
| | |
|---|---|
| *A61B 17/11* | (2006.01) |
| *A61B 17/115* | (2006.01) |
| A61B 17/00 | (2006.01) |
| A61B 17/22 | (2006.01) |
| A61B 17/30 | (2006.01) |
| A61F 2/04 | (2013.01) |

(56) References Cited

U.S. PATENT DOCUMENTS

| | | | |
|---|---|---|---|
| 3,828,782 A | 8/1974 | Polin | |
| 4,368,739 A | 1/1983 | Nelson, Jr. | |
| 4,573,966 A | 3/1986 | Weikl et al. | |
| 4,905,693 A | 3/1990 | Ravo | |
| 5,007,437 A | 4/1991 | Sterzer | |
| 5,074,868 A | 12/1991 | Kuzmak | |
| 5,152,277 A | 10/1992 | Honda et al. | |
| 5,443,445 A * | 8/1995 | Peters | A61M 3/0283 604/27 |
| 5,569,216 A | 10/1996 | Kim | |
| 5,620,457 A | 4/1997 | Pinchasik et al. | |
| 5,820,595 A | 10/1998 | Parodi | |
| 6,068,636 A | 5/2000 | Chen | |
| 6,082,855 A * | 7/2000 | Fleming | A61F 9/029 351/123 |
| 6,299,598 B1 | 10/2001 | Bander | |
| 6,575,932 B1 | 6/2003 | O'Brien et al. | |
| 6,576,429 B1 | 6/2003 | Haellgren | |
| 7,846,132 B2 | 12/2010 | Gravesen et al. | |
| 8,216,159 B1 | 7/2012 | Leiboff | |
| 8,690,817 B2 | 4/2014 | Assaf et al. | |
| 2001/0049497 A1 | 12/2001 | Kalloo et al. | |
| 2002/0077594 A1 | 6/2002 | Chien et al. | |
| 2002/0188282 A1 | 12/2002 | Greenberg | |
| 2003/0050662 A1 | 3/2003 | Don Michael | |
| 2003/0069472 A1 | 4/2003 | Butler | |
| 2003/0187428 A1 | 10/2003 | Lane et al. | |
| 2004/0153167 A1 | 8/2004 | Stack et al. | |
| 2004/0243057 A1 | 12/2004 | Vinten-Johansen | |
| 2005/0033226 A1 * | 2/2005 | Kim | A61F 2/0013 604/101.01 |
| 2005/0038374 A1 | 2/2005 | Williams, Jr. et al. | |
| 2005/0080437 A1 | 4/2005 | Wright | |
| 2005/0197531 A1 | 9/2005 | Cabiri et al. | |
| 2005/0197664 A1 | 9/2005 | Blomme | |
| 2005/0277945 A1 | 12/2005 | Saadat et al. | |
| 2006/0167538 A1 * | 7/2006 | Rucker | A61F 2/04 623/1.25 |
| 2007/0118157 A1 | 5/2007 | Zuidema et al. | |
| 2007/0250084 A1 | 10/2007 | Sharkawy et al. | |
| 2008/0103442 A1 * | 5/2008 | Kesten | A61M 25/1002 604/96.01 |
| 2008/0146869 A1 | 6/2008 | Chow et al. | |
| 2008/0183202 A1 | 7/2008 | Isham | |
| 2008/0221597 A1 | 9/2008 | Wallace et al. | |
| 2009/0062608 A1 | 3/2009 | Miyoshi | |
| 2009/0062717 A1 | 3/2009 | Laufer | |
| 2009/0093767 A1 * | 4/2009 | Kelleher | A61F 2/04 604/175 |
| 2009/0099546 A1 | 4/2009 | Macy, Jr. | |
| 2009/0149880 A1 | 6/2009 | Gobel | |
| 2009/0216337 A1 | 8/2009 | Egan et al. | |
| 2009/0270955 A1 | 10/2009 | Magers et al. | |
| 2009/0275889 A1 | 11/2009 | Ravikumar | |
| 2009/0326490 A1 | 12/2009 | McMichael et al. | |
| 2010/0010519 A1 | 1/2010 | Stopek et al. | |
| 2010/0016871 A1 | 1/2010 | Brooks et al. | |
| 2010/0022976 A1 | 1/2010 | Weig | |
| 2010/0023132 A1 | 1/2010 | Imran | |
| 2010/0076470 A1 | 3/2010 | Elachchabi et al. | |
| 2010/0105983 A1 | 4/2010 | Oneda et al. | |
| 2010/0191264 A1 | 7/2010 | Kassab et al. | |
| 2010/0256775 A1 | 10/2010 | Belhe et al. | |
| 2010/0268154 A1 | 10/2010 | Vining | |
| 2010/0286753 A1 | 11/2010 | Zelickson et al. | |
| 2010/0305503 A1 | 12/2010 | Fang et al. | |
| 2010/0312272 A1 | 12/2010 | Pavcnik et al. | |
| 2011/0009690 A1 | 1/2011 | Belhe et al. | |
| 2011/0015571 A1 | 1/2011 | Voss et al. | |
| 2011/0040231 A1 * | 2/2011 | Gregory | A61F 5/445 604/8 |
| 2011/0137428 A1 | 6/2011 | Terliuc | |
| 2011/0160657 A1 | 6/2011 | Goebel | |
| 2011/0208139 A1 | 8/2011 | Kim et al. | |
| 2011/0218493 A1 | 9/2011 | Miyasaka et al. | |
| 2011/0245752 A1 | 10/2011 | Levine et al. | |
| 2011/0295288 A1 | 12/2011 | Khosrovaninejad | |
| 2011/0306823 A1 | 12/2011 | Goebel et al. | |
| 2012/0078029 A1 | 3/2012 | Subramanian | |
| 2012/0095432 A1 | 4/2012 | Nath | |
| 2012/0232459 A1 | 9/2012 | Dann et al. | |
| 2012/0239076 A1 | 9/2012 | Cisko, Jr. | |
| 2012/0253204 A1 | 10/2012 | Ben-Yehuda | |
| 2012/0310138 A1 | 12/2012 | Behan | |
| 2013/0158463 A1 | 6/2013 | Assaf et al. | |
| 2015/0045715 A1 | 2/2015 | Assaf et al. | |

FOREIGN PATENT DOCUMENTS

| | | |
|---|---|---|
| EP | 1298477 | 4/2003 |
| JP | 08-112359 | 5/1996 |
| JP | H 08112359 | 5/1996 |
| JP | 09-038197 | 2/1997 |
| JP | 09-038198 | 2/1997 |
| JP | H 09038197 | 2/1997 |
| JP | H 09038198 | 2/1997 |
| JP | 2000-014767 | 1/2000 |
| JP | 2000-325483 | 11/2000 |
| JP | 2001-170164 | 6/2001 |
| JP | 2002-065595 | 3/2002 |
| JP | 2002-065844 | 3/2002 |
| JP | 2005-519709 | 7/2005 |
| WO | WO 03/086507 | 10/2003 |
| WO | WO 2007/059490 | 5/2007 |
| WO | WO 2007/140559 | 12/2007 |
| WO | WO 2009/046998 | 4/2009 |
| WO | WO 2012/081005 | 6/2012 |
| WO | WO 2012/148727 | 6/2012 |
| WO | WO 20121081005 | 6/2012 |
| WO | WO 2012/148727 | 11/2012 |
| WO | WO 2016/059634 | 4/2016 |

OTHER PUBLICATIONS

Notice of Reason for Rejection Dated Jul. 21, 2015 From the Japanese Patent Office Re. Application No. 2013-543966.
Corrected Notice of Allowability Dated Jan. 14, 2014 Re. U.S. Appl. No. 13/769,338.
International Preliminary Report on Patentability Dated Jun. 27, 2013 From the International Bureau of WIPO Re. Application No. PCT/IL2011/000934.
International Search Report and the Written Opinion Dated May 21, 2012 From the International Searching Authority Re. Application No. PCT/IL2011/000934.
Notice of Allowance Dated Dec. 26, 2013 From the US Patent and Trademark Office Re. U.S. Appl. No. 13/769,338.
Official Action Dated Sep. 10, 2013 From the U.S. Patent and Trademark Office Re. U.S. Appl. No. 13/769,338.
Official Action Dated May 23, 2013 From the US Patent and Trademark Office Re. U.S. Appl. No. 13/769,338.

(56) References Cited

OTHER PUBLICATIONS

International Search Report and Written Opinion issued in International Patent Application No. PCT/IL2011/000934, mailed May 21, 2012 (12 pages).
International Preliminary Report on Patentability issued in International Patent Application No. PCT/IL2011/000934, mailed Jun. 27, 2013 (8 pages).
Notification of Office Action and Search Report Dated Jul. 15, 2015 From the State Intellectual Property Office of the People's Republic of China Re. Application No. 201180060468.4.
Translation of Notice of Reason for Rejection Dated Jul. 21, 2015 From the Japanese Patent Office Re. Application No. 2013-543966.
Translation of Notification of Office Action Dated Jul. 15, 2015 From the State Intellectual Property Office of the People's Republic of China Re. Application No. 201180060468.4.
Notice of Reason for Rejection Dated Feb. 2, 2016 From the Japanese Patent Office Re. Application No. 2013-543966.
Translation Dated Feb. 16, 2016 of Notice of Reason for Rejection Dated Feb. 2, 2016 From the Japanese Patent Office Re. Application No. 2013-543966.
Office Action Dated Apr. 21, 2016 From the Israel Patent Office Re. Application No. 226843 and Its Translation Into English.
Pre-Appeal Examination Report Dated May 26, 2016 From the Japanese Patent Office Re. Application No. 2013-543966 and Its Translation Into English.

\* cited by examiner

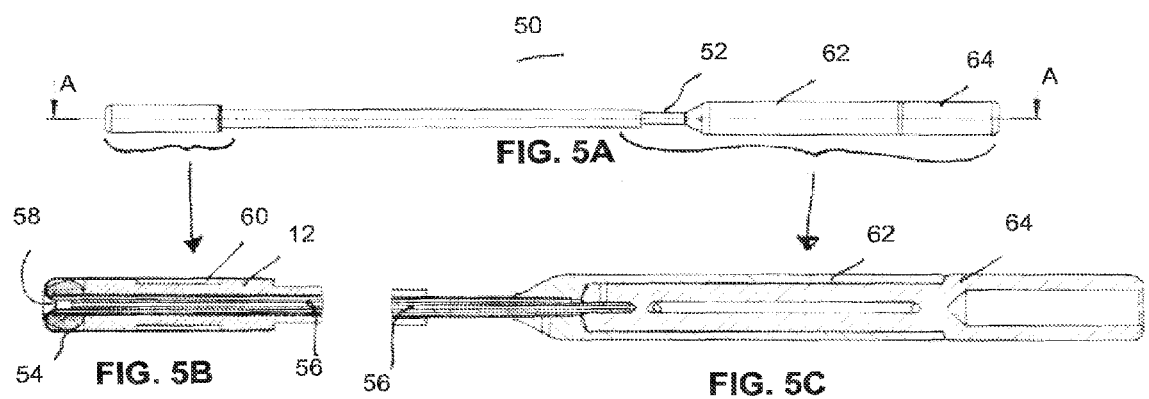

SYSTEMS AND METHOD FOR BYPASSING AN ANASTOMOSIS SITE

RELATED APPLICATIONS

This application is a continuation of U.S. application Ser. No. 13/769,338, filed on Feb. 17, 2013, which is a Continuation-in-Part of International Patent Application No. PCT/IL2011/000934, filed Dec. 8, 2011, which claims the benefits of priority to U.S. Provisional Patent Application Nos. 61/423,529, filed Dec. 15, 2010, and 61/524,343, filed Aug. 17, 2011. Each of these applications is herein incorporated by reference in their entireties.

FIELD AND BACKGROUND OF THE INVENTION

The present invention relates to a system and method for bypassing an anastomosis site in a hollow organ, such as, for example, a colon. Embodiments of the present invention relate to systems which include an intra-luminal sheath for bypassing an anastomosis site and an external element which serves to limit movement of the intra-luminal sheath within the hollow organ such that a portion of the intra-luminal sheath resides upstream of the anastomosis site.

Surgical intervention can require an operative union of resected tissues or a bypass of non-resected diseased tissue. Such union procedures, which are termed anastomosis, can be performed via open or minimal invasive surgery where the ligated ends are manually sutured or stapled using a surgical stapler. While an anastomosis may be end-to-end, it could also be performed side-to-side or end-to-side depending on the required reconstruction or bypass. Anastomosis can be performed on vascular structures, the gastrointestinal (GI) tract (including esophagus, stomach, small bowel, large bowel, bile ducts, and pancreas), and the urinary tract (including ureters, urinary bladder and urethra).

An anastomosis is a common procedure, in particular in the gastrointestinal (GI) tract. Virtually all elective resections of gastrointestinal organs are followed by anastomoses to restore continuity; pancreaticoduodenectomy is considered a massive operation, in part, because it requires three separate anastomoses (stomach, biliary tract and pancreas to small bowel). The widespread use of mechanical suturing devices (linear and circular staplers) radically altered gastrointestinal surgery in the last decade.

Although commonly performed, GI anastomosis carry a relatively high risk of anastomotic leaks especially in subjects that are immuno-compromised, such as subjects undergoing chemotherapy. Such leaks must be identified in a reasonable amount of time to allow for medical intervention.

In order to address the problem of anastomotic leaks, several internal sheaths which bypass the anastomotic site have been devised (see U.S. Pat. Nos. 4,905,693 and 6,068,636 and U.S. Patent Application Publication No. 2007/0118157). Such sheaths are typically anchored above (upstream) the anastomotic site thereby enabling the flow of material to circumvent or bypass the anastomosis site.

Although these solutions appear to be promising, anchoring of the sheath to the intraluminal wall via staples, sutures or stent-like rings has the potential of causing tissue trauma and complications during sheath placement and removal.

While reducing the present invention to practice, the present inventors have devised a bypass system which includes an intra-luminal sheath which is maintained upstream of the anastomosis site via a movement-limiting element positioned outside the anastomosed organ, thereby minimizing tissue trauma during positioning and removal.

SUMMARY OF THE INVENTION

According to one aspect of the present invention there is provided a system for bypassing an anastomosis site in a hollow organ comprising: (a) a shielding device configured for spanning the anastomosis site at an internal surface of the hollow organ; (b) an element configured for attachment to an external surface of the hollow organ and limiting migration of said shielding device beyond the anastomosis site.

According to further features in preferred embodiments of the invention described below, the shielding device is a tubular sleeve.

According to still further features in the described preferred embodiments the tubular sleeve includes a first tubular region having a diameter larger than that of a contiguous second tubular region, optionally such an increased diameter is achieved via an expandable structure e.g. one that includes at least one toroidal balloon.

According to still further features in the described preferred embodiments the element is a band encircling the external surface of the hollow organ, the band being sized so as to prevent migration of the first tubular region beyond a region of the hollow organ encircled by the band.

According to still further features in the described preferred embodiments the first tubular region is more rigid than the second tubular region.

According to still further features in the described preferred embodiments the band does not apply a substantial inward radial force to tissue of the external surface of the hollow organ.

According to still further features in the described preferred embodiments a diameter of the band equals to, or is greater than, a diameter of the hollow organ.

According to still further features in the described preferred embodiments the first tubular region includes an inflatable cuff/balloon.

According to still further features in the described preferred embodiments the tubular sleeve includes a fluid conduit for inflating the inflatable cuff from an end of the second tubular region.

According to still further features in the described preferred embodiments the shielding device includes a fluid conduit for injecting an agent into the hollow organ.

According to still further features in the described preferred embodiments the agent is a contrast dye.

According to still further features in the described preferred embodiments the agent is a bioadhesive or any material that is capable of repairing/healing tissue.

According to still further features in the described preferred embodiments the element and/or the shield are at least partially fabricated from a bio-absorbable material.

According to still further features in the described preferred embodiments the band includes an adjustment mechanism for adjusting a diameter thereof.

According to still further features in the described preferred embodiments the adjustment mechanism includes a string encircling the band.

According to still further features in the described preferred embodiments the string is provided within a tube encircling the band.

According to still further features in the described preferred embodiments an internal surface of the band is fabricated from a polymer having a Shore A value of 5-60.

According to still further features in the described preferred embodiments the second tubular region is fabricated from a polymer having a Shore A value of 5-60.

According to still further features in the described preferred embodiments the tubular sleeve and the element are configured for use in bypassing anastomosis of a colon.

According to still further features in the described preferred embodiments the band is constructed from a linear strip closable to a circle via the adjustment mechanism.

According to another aspect of the present invention there is provided a method of internally shielding an anastomosis site in a hollow organ comprising: (a) positioning an element at an external surface region of the hollow organ displaced from the anastomosis site; (b) positioning a shielding device at an internal region of the hollow organ spanning the anastomosis site; and (c) deploying the shielding device and/or the element to prevent a portion of the shielding device from migrating passed an internal region of the hollow organ corresponding to the external surface region thereby internally shielding the anastomosis site in the hollow organ.

According to still further features in the described preferred embodiments the element is a band encircling the external surface region of the hollow organ and the shielding device is a tubular sleeve.

According to still further features in the described preferred embodiments (c) results in that the portion of the tubular sleeve has a diameter larger than that of the band.

According to still further features in the described preferred embodiments the hollow organ is a colon and further wherein (a) is effected by delivering the shielding device through the anal orifice.

According to still further features in the described preferred embodiments (a) is effected by closing a linear strip into the band around the external surface region of the hollow organ.

According to still further features in the described preferred embodiments (c) is effected at least in part by inflating the portion of the tubular sleeve.

According to still further features in the described preferred embodiments (c) is effected at least in part by constricting the band.

According to still further features in the described preferred embodiments the inflating is effected via an inflation conduit having an inflation port positioned outside the body.

According to still further features in the described preferred embodiments the shielding device extends through the colon from a region above the anastomosis site to outside the anal orifice when deployed.

According to still further features in the described preferred embodiments the band encircles the external surface region of the hollow organ without applying substantial inward radial force to tissue of the external surface of the hollow organ.

The present invention successfully addresses the shortcomings of the presently known configurations by providing a bypass system which can be used to bypass an anastomosis site of a hollow organ such as a colon without requiring in tissue anchoring.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 5A-C illustrate a delivery apparatus for delivering the present tubular sleeve component into a hollow organ. FIGS. 5B-C are magnified views of distal and proximal regions of the apparatus shown in FIG. 5A.

DESCRIPTION OF THE PREFERRED EMBODIMENTS

Figure 1A:
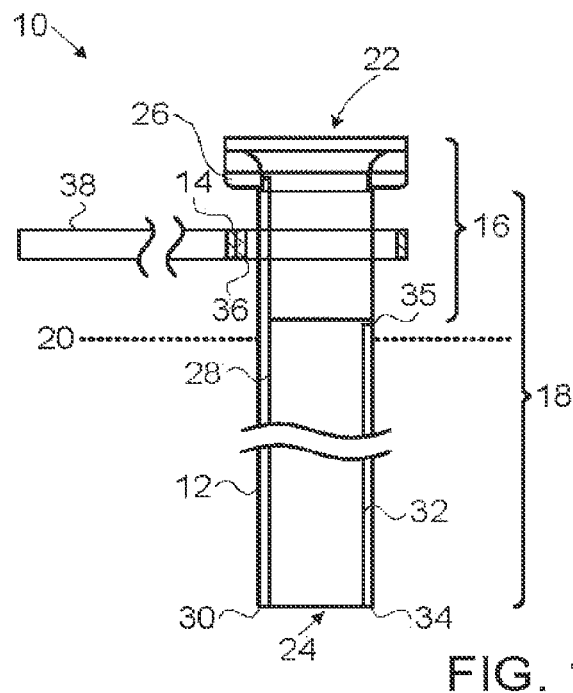
FIGS. 1A-B are side (FIG. 1A) and perspective (FIG. 1B) views of one embodiment of the present system.
Figure 1B:
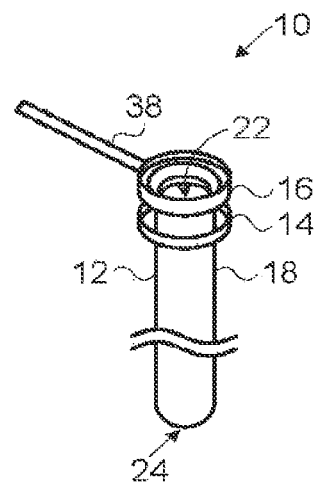

The present invention is of a system which can be used to bypass an anastomosis site in a hollow organ. Specifically, the present invention can be used to bypass an anastomosis site in a hollow organ such as a colon by utilizing an intraluminal shield and maintaining it in position across the anastomosis site via an external movement limiting element.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Leaks from anastomosis sites are a major complication of surgical union of hollow organ tissues. In fact, the rate and clinical implications of anastomotic leakage in colorectal and colo-anal anastomosis oftentimes necessitates a loop stoma for fecal diversion.

To address this problem, anastomosis protection devices for internally bypassing an anastomosis site have been developed. Such protection devices employ internally anchored sleeves (e.g. U.S. 20100010517, U.S. 20100010518) or externally clamped sleeves (e.g. U.S. Pat. No. 3,435,823, U.S. 20050033226) for routing feces and isolating it from the anastomosis site. Although such devices provide a promising alternative to fecal diversion procedures, they have yet to meet clinical acceptance largely due to complications associated with sleeve-tissue anchoring and sleeve placement and removal.

To address these problems, the present inventors have devised an anastomosis bypass system which simplifies sleeve positioning while substantially reducing the potential for tissue trauma and complications during sleeve placement and removal.

As is further described hereinunder, the present system employs an intraluminal shield (preferably shaped as a tubular sleeve) and an externally mounted sleeve movement-limiting element (preferably configured as a band) which limits the shield from moving past the anastomosis site. As is demonstrated by the results shown in the Examples section, use of such a system in bypassing an anastomosis site of a colon resulted in no detected movement of the sleeve portion and no substantial tissue trauma during positioning, use and removal.

Thus, according to one aspect of the present invention there is provided a system for bypassing an anastomosis site of a hollow organ.

As used herein, the phrase "hollow organ" refers to any hollow tissue structure that serves as a conduit for biological material. Examples include the GI tract, including the esophagus, stomach and intestines, the urinary tract, including the ureters, bladder and urethra, and the vascular system including arteries, veins and the like. As used herein, the phrase biological material includes, but is not limited to, feces, urine, blood and the like.

The system includes a shielding device configured for spanning the anastomosis site at an internal surface of the hollow organ and an element (also termed herein as "movement-limiting element") which is configured for positioning outside an external surface of the hollow organ and limiting migration of the shielding device beyond the anastomosis site.

The shielding device can be configured in any shape and dimension suitable for partially or fully covering the intraluminal surface of the anastomosis site and minimizing leakage therefrom.

When fully deployed the shielding device can be configured as a partially or fully closed tubular structure fabricated from a single sheet of material or several overlapping or spaced apart longitudinal strips of material. Alternatively, the shielding device can be shaped as a set of interlocked (e.g. telescoping) tubes.

One presently preferred configuration of a shielding device is a closed tubular sleeve constructed from silicon, PTFE, Dacron™ or latex or any other suitable material and having dimensions in the range of 250-500 mm length, 25-50 diameter and 0.05-1 mm wall thickness.

The sleeve includes an upstream opening (also referred to herein as "distal opening") for receiving the biological material transported through the hollow organ and downstream opening (also referred to herein as "proximal opening") which serves as an exit point for the biological material.

The sleeve can be fabricated using molding, spinning or extrusion using approaches well known in the art.

The sleeve can include two distinct functional portions. A first portion (also referred to herein as "upstream/distal portion") functions in stabilizing the sleeve within the hollow organ and sealing it with respect to the hollow organ inner walls, thus serving as the entry portion for the biological material. As such the first portion is preferably more rigid in nature and can be shaped to facilitate movement of the biological material from the hollow organ and into the sleeve. The first portion of the sleeve is preferably constructed from silicon (Shore A 30-80), with a thickness of 0.1-0.6 mm and configured with an external diameter of 30-60 mm, and a length of 25-100 mm. As is further described hereinunder, this portion can also include stabilizing struts and inflatable external balloons for anchoring and stabilization. Although the diameter of the first portion can increase slightly under internal pressure exerted by passage of biological material, such increase is typically no more than 5-15% of the fully open diameter.

A second (and preferably contiguous) portion of the sleeve (also referred to herein as "downstream/proximal portion") can function in directing the biological material moving through the sleeve into a portion of the hollow organ downstream of the anastomosis site and/or outside the body.

As such, this portion of the sleeve is designed to contain the biological material while providing some accommodation for volume and movement. The second portion of the sleeve can be elastic and flimsy and is preferably constructed from a silicon material (Shore A value of 5-40) and a thickness of 0.05-0.3 mm. Depending on the anastomosis bypassed, the second portion of the sleeve can range in length from 150-450 mm and 20-40 mm in diameter when fully open. For example, when utilized in bypassing a low colorectal anastomosis, the second portion of the sleeve can be 150-350 in length when fully deployed.

The presently preferred sleeve configuration includes a first portion which is contiguous with a second portion and is thus fabricated as one unitary structure or assembled from two irreversibly attached portions (using for example, adhesives, mechanical fasteners and the like) which are assembled prior to positioning. However, the present invention also envisages a configuration in which the two portions are separately positioned and then connected via sutures, staples, glue and the like.

The first portion can also include a mechanism for further stabilizing the sleeve in the hollow organ and limiting its movement against the externally mounted movement-limiting element.

Such a mechanism can include an expandable structure which can be used for increasing the external diameter of the first portion following deployment. Examples include, stent-like bands which are expanded following deployment, compressed foam-like elements (disposed as a ring or discrete 'blocks' around the outer circumference of the first portion).

Expansion of such mechanisms can be effected by releasing a constraining mechanism such as a sheath or a pull-string. For example, a stent like band (cut out of a Nitinol or stainless steel tube or braided from Nitinol or stainless steel wire) initially shaped to about 50 mm outer diameter (OD) is compressed into a sheath with 10 mm internal diameter (ID); once released from the sheath, the stent-like band will elastically expand to the original 50 mm diameter.

A presently preferred expandable structure includes one or more inflatable structures (balloons/bladders/sacs) disposed as a ring or a plurality of discrete inflatable structures around the outer circumference of the first portion.

Inflation of such an inflatable structure can be effected via an inflation conduit disposed within a sidewall of the sleeve. Depending on the anastomosis bypassed, such conduit can run the length of the sleeve from the distal opening to the inflatable structure(s), or it can traverses only a portion of this length (e.g. 100-400 mm).

As is mentioned above, the system of the present invention also includes a movement-limiting element for limiting the movement of the sleeve and preventing the first portion thereof from migrating past the anastomosis site (in a direction of flow through the hollow organ).

Several alternative configuration of a movement-limiting element are envisaged herein.

The presently preferred configuration of a movement-limiting element is a band encircling the outer surface of the hollow organ. It will be appreciated that such a band need not completely encircle the hollow organ; as such it can be an open band covering, for example, 270 degrees of the circumference of the hollow organ.

A presently preferred configuration of the band is configured such that no substantial force is applied to the hollow organ when in use. Such a configuration negates the possibility of tissue ischemia and necrosis especially when the hollow organ is, for example, a colon which distends when fecal matter passes therethrough.

A hollow organ such as a colon is designed to radially expand in order to accommodate passage of feces during peristalsis. Such expansion can increase the diameter of a colon from 3 to 6 cm. A band positioned in close contact with the outer wall of the colon can apply substantial inward pressure on the wall tissue when the colon expands during passage of feces. Such pressure can lead to tissue ischemia and necrosis and or to tissue erosion dues to both compressive forces and axial forces and frictional forces that result from axial movement of the colon with respect to the band.

To solve this problem, the band of the present invention can be configured to closely encircle the hollow organ and elastically expand when the organ expands, or alternatively and preferably the band can be configured with a diameter slightly smaller than that of the expanded organ (e.g. about 15-30% smaller), but larger than that of the relaxed state of the hollow organ (e.g. about 15-30% larger). In the case of colon anastomosis, the band can be fabricated with an internal diameter of 30-50 mm and a substantially rigid (non-elastic) internal circumflex. Since the distal portion of the (internal) sleeve is relatively rigid (as described above), it may limit organ radial expansion at the site around and distally to the anastomosis and thus reduce contact forces between the organ outer wall and the band inner diameter.

The band limits movement of the sleeve (specifically the first portion of the sleeve) by functioning as a stop for the first portion of the sleeve (e.g. a stop for the balloon or balloon inflated around the first portion of the sleeve).

For example, a band having an internal diameter of 40 mm would function as a movement stop for a sleeve which includes a first portion having an external diameter of 50 mm and yet such a band would not apply compressive forces to the outer colon wall.

In order to limit migration of the sleeve downstream past the anastomosis site, the band is preferably located at or above the anastomosis site. To prevent migration, the band is secured to the tissue at the desired site via anchors, adhesive, sutures and the like. Such securement can be to the outer wall of the hollow organ or to tissues adjacent thereto. In the case of colorectal anastomosis, the band can be located about 50-100 mm above the anastomosis and axially secured in place by threading the band through the colon mesentery.

The band is delivered as a linear strip and closed to a circle around the hollow organ using, for example, a latch, a suture, a lasso suture around the band or other locking mechanisms. Delivery of the band is preferably effected through an incision in the abdominal wall. The diameter of the band can be adjustable prior to or following positioning using, for example, a ratchet concept in which the relatively stiff outer rim of the band is tuned and locked to a diameter that will allow the above defined gap between the colon and the internal "relatively soft" inner band material or a Lasso concept in which the diameter of the ring is limited (and changed) by a "suture" going around the soft inner ring material. In that concept shortening of the suture length will decrease the ring OD.

Thus, the present invention provides an anastomosis bypass system which enables easy and rapid deployment of a bypass sleeve inside a hollow organ and employs a sleeve movement-limiting element that substantially reduces the chance of tissue trauma during positioning, use and removal of the system.

The system of the present invention provides the following features:

(i) provides an internal bypass of anastomosis site without in-tissue anchoring;

(ii) prevents leakage from anastomosis site by completely shielding internal tissue wall at the site of anastomosis from biological material;

(iii) can be easily deployed and positioned during or following the anastomosis procedure;

(iv) enables anastomosis leakage testing during the procedure and prior to bypass removal;

(v) bypass is fully functional immediately following anastomosis procedure; and (vi) enables removal of system components without tissue trauma or use of invasive procedures.

Referring now to the drawings, FIGS. 1a-5c illustrate several preferred embodiments of the present system which is referred to herein as system 10.

System 10 of FIGS. 1a-5c is configured for use in colorectal anastomosis and thus is sized and configured appropriately. It will be appreciated that configurations suitable for use in bypassing an anastomosis in other hollow organs (e.g. of the vascular or urinary systems) are also envisaged herein.

System 10 includes a tubular sleeve 12 (shown separately in FIGS. 2a-c) which is sized and configured for positioning within a lumen of a colon across the anastomosis site; and a band 14 (also shown in FIGS. 4a-e) which is sized and configured for placement around the outer surface of the colon.

Sleeve 12 includes a first portion 16 and a contiguous second portion 18. Sleeve 12 is fabricated by fitting a pliable tube (e.g. silicon, Shore A value of 10-30) having a length of 250-450 mm and a outer diameter of 25-30 mm over a more rigid tube (silicon Shore A value of 30-80) having a length of 60-100 mm, and an outer diameter of about 25-30 mm.

Sleeve 12 includes a distal opening 22 which is shaped as a trumpet in order to facilitate passage of feces from the colon and into sleeve 12. Sleeve 12 also includes proximal opening 24 for allowing the feces transported through sleeve 12 to exit into the colon downstream of sleeve 12 or directly outside the body. A distal portion 18 having sufficient length (e.g. 250-450 mm) to traverse the lower GI such that proximal opening 24 is positioned outside the body (outside the anal orifice) is presently preferred for colorectal anastomosis bypass.

Sleeve 12 is positioned inside the colon such that first portion 16 resides upstream of anastomosis site (indicated by dotted line 20 In FIG. 1a) while second portion 18 resides downstream of the anastomosis site.

Figure 3A:
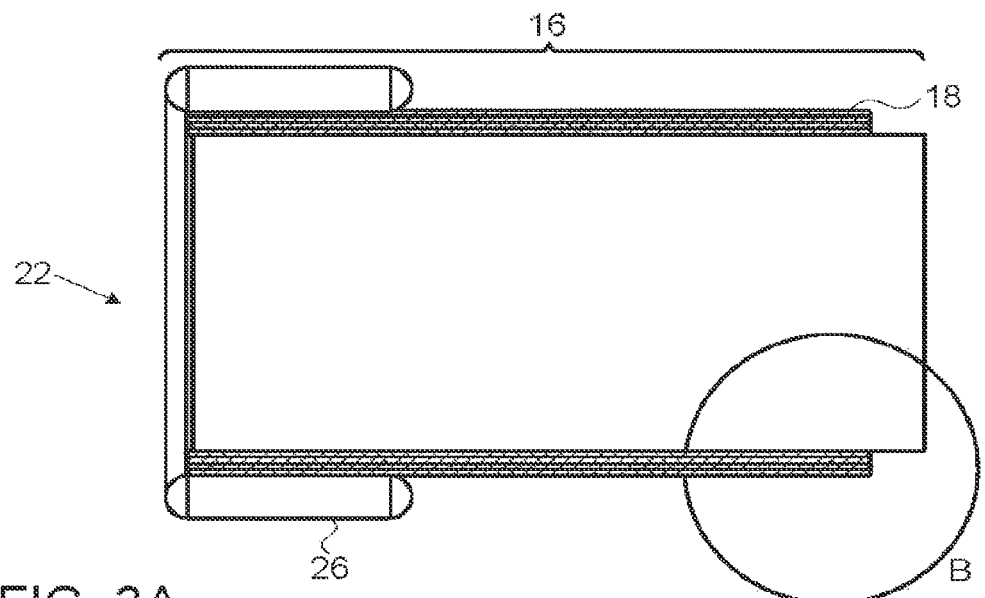
FIGS. 3A-B illustrate another embodiment of the tubular sleeve which is internally folded and suitable for delivery prior to anastomosis.
Figure 3B:
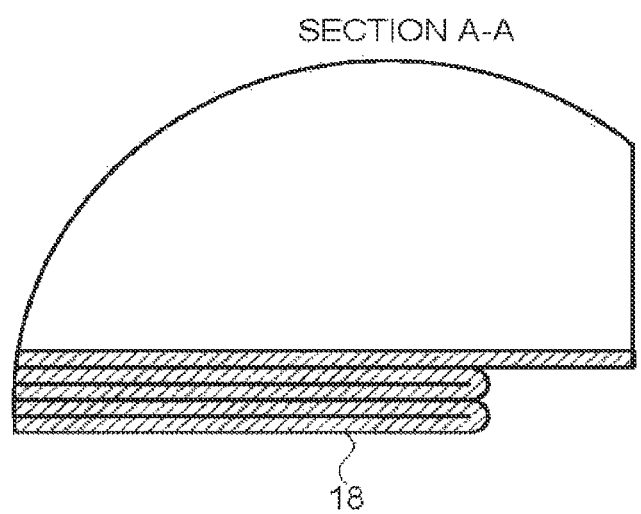

The configuration of sleeve 12 shown in FIGS. 3a-b includes an option of folding second portion 18 into first portion 16. This option is useful in procedures that include a step of positioning sleeve 12 prior to anastomosis, such as that described below with reference to FIGS. 14-18. Proximal end of folding section 18 can include a set of connectors that can be attached to the tip of the stapler and thus allow deployment (unfolding) of section 18 when the stapler is pulled out.

Sleeve 12 further includes an inflatable balloon 26 which when inflated secures sleeve 12 in position and provides security against migration of sleeve 12 past band 14 by increasing the outer diameter of first portion 16. Balloon 26 is inflated (with gas or a liquid) following positioning of sleeve 12 in the colon via fluid conduit 28 which fluidly connects filling port 30 to balloon 26. Filling port can include a one way valve having, for example, a duckbill configuration or any other valve design known in the art. Sleeve 12 may further include a second fluid conduit 32 which connects a second fluid filling port 34 to a discharge port 35 opening at an external surface of sleeve 12. Fluid conduit 32 can be used to deliver a contrast material, or a dye from outside the body to the site of anastomosis when sleeve 12 is in position. Delivery of such a dye can be used to identify leaks in the anastomosis site. Fluid conduit 32 can also be used to deliver a bioadhesive such as fibrin glue or a tissue repair agent, such as keratinocyte growth factor (FGF-7) in order to facilitate healing of the anastomosis site. Discharge port 35 can be single port or a set connected ports radially located around the tube.

Figure 2A:
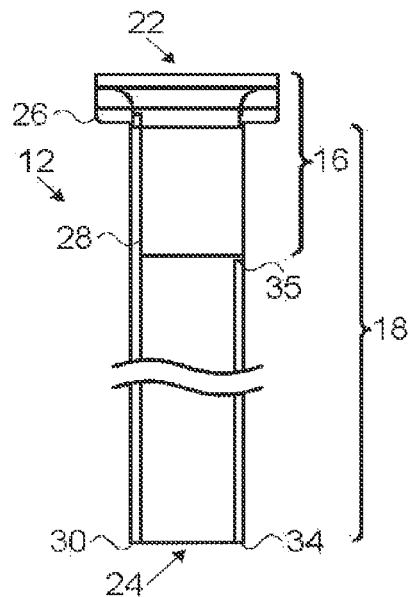
FIGS. 2A-B are side (FIG. 2A) and perspective (FIG. 2B) views of one embodiment of the tubular sleeve component of the present system.
Figure 2B:
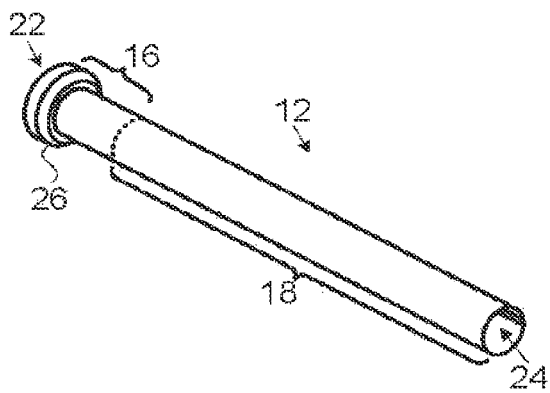
Figure 2C:
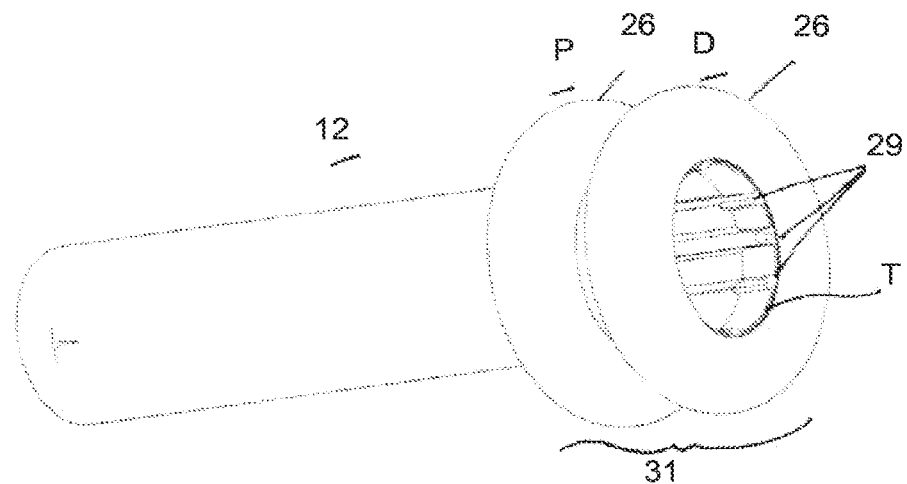
FIG. 2C-D are isometric views of a sleeve including two balloons (FIG. 2C) and a sleeve including three balloons (FIG. 2D).
Figure 2D:
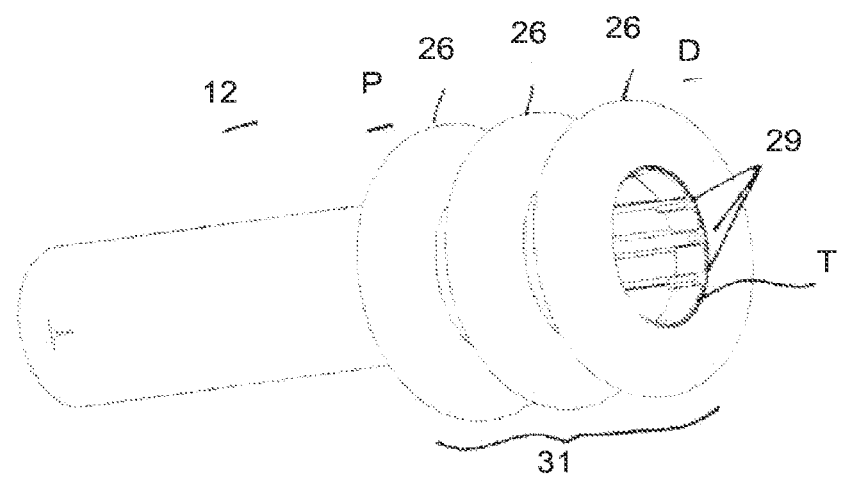

FIG. 2c-d illustrate an embodiments of sleeve 12 which include two (FIG. 2c) or three (FIG. 2d) balloons 26. Balloons 26 serve to minimize rotation of sleeve 12 and in particular legion 31 thereof in a hollow organ. While experimenting with several configurations, the present inventor have uncovered that a sleeve 12 having a single balloon 26 can at times rotate (yaw) within the hollow organ. Although a single balloon having a length spanning region 31 can be used to prevent such rotation, a two or three balloon configuration greatly enhances anchoring, sealing and facilitates deployment of sleeve 12 within hollow organ. Each balloon 26 has a diameter of 40-60 mm and a section diameter of 6-30 mm; region 31 is typically 1-2 times the diameter of balloon 26 e.g. 40-120 mm.

In order to longitudinally stiffen the distal portion of sleeve 12 and yet maintain radial compliance, region 31 of sleeve 12 can be thickened (at the region of balloons 26, as indicated by T) or fabricated from a material having increased rigidity (e.g. higher Shore value) or it can preferably include struts 29 which are attached via adhesive to an inner surface of sleeve 12 at region 31 or co-molded therewith (e.g. overmolding sleeve 12 over struts 29).

Struts 29 can be fabricated from an alloy such as stainless steel or Nitinol or from a polymer such as silicone, polyamide, nylon etc. Struts 29 can be 40-150 mm long and 0.25-1 mm in diameter.

Stiffening region 31 can also be effected using a stent-like structure laser cut from a tube or braided from wire.

Proximal balloon 26 (P) functions in preventing axial movement of sleeve 12 by acting as a stop against external band 14 (as described below), while Distal balloon 26 (D) enhances anchoring, stability and sealing of sleeve 12 in the hollow organ. Struts 29 structurally interconnect balloons 26 at region 31 and as a result enable greater resistance to sleeve rotation (torsion).

Band 14 of system 10 can be fabricated from a linear strip (FIG. 4d)) that is closed to assume a circular configuration (FIGS. 4a-c and 4e) and can be adjusted for proper diameter by using lock mechanism 36 and actuation string 40.

Band 14 can be fabricated from silicon, polyurethane or a biodegradable material such as polyglactin or others and includes a housing 39 with an internal tract through which a suture 42 is threaded to be locked and secured on it distal side by lock mechanism 36. Pulling on the ends of suture 42 reduces the diameter of band 14; activation of mechanism 36 locks suture 42 and thus locks band 14 at the desired diameter. Deactivating lock mechanism 36 releases by pulling suture 40 thus relaxing band 14 to its original diameter (elastic relaxation) and farther deactivating will completely release suture 42 and allow for band 14 opening. Adjustment and release mechanism via sutures 40 and 42 can be activated/deactivated via handle 38 which extends from band 14 outside the body.

When in the circular configuration, band 14 surrounds the colon upstream of the anastomosis site and is anchored in place by threading the linear strip through the colon mesentery and around the colon and closing it to the circular configuration shown in the Figures.

Band 14 is adjusted to an internal diameter of 35-50 mm such that it applies little or no inward radial pressure (0-0.15 Atm) on the colon when the colon expands during passage of soft feces (as is the case following colectomy).

Band 14 can also be fixed in diameter, in which case, the user can choose from different size bands 14. The diameter of an anastomosed site is typically in the range of 20-25 mm. As a result, the portion of sleeve 12 that traverses the stapled area cannot be much larger than 30 mm in diameter (also the colon ID above and below the anastomosis). Migration of sleeve 12 is prevented by band 14, thus, as long as the OD of balloon 26 is larger than the ID of band 14, sleeve 12 cannot migrate passed band 14. Typical dimensions for a fixed diameter band 14 are: ID 35-50 mm and OD 40-60 mm.

Figure 4A:
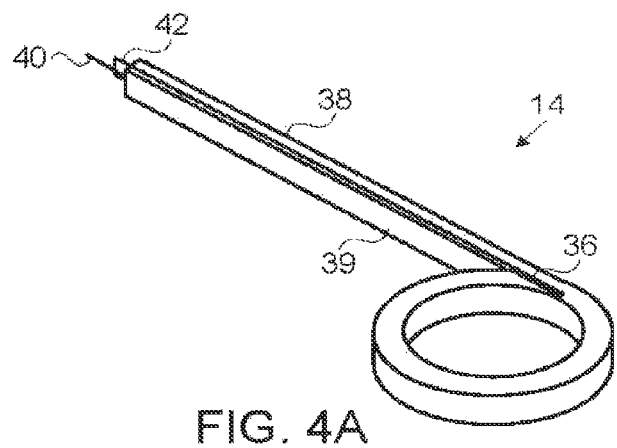
FIGS. 4A-C are side (FIG. 4A) and perspective (FIG. 4B-C) views of embodiments of the band component of the present system.
Figure 4B:
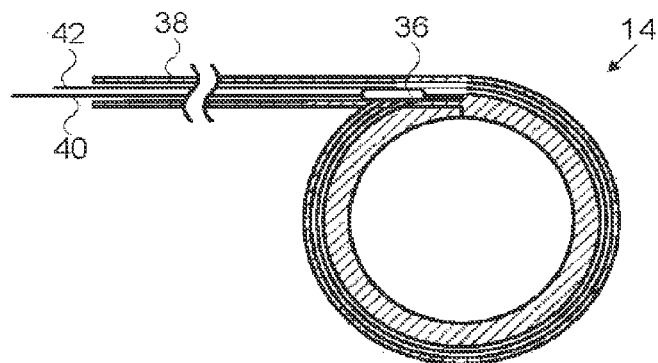
Figure 4C:
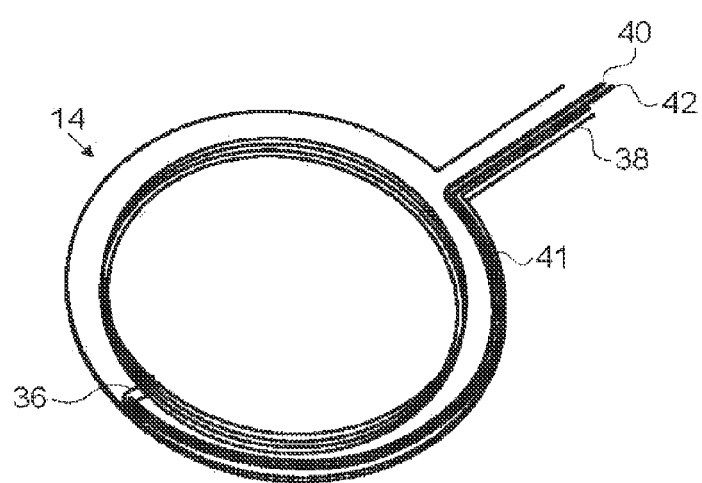

FIG. 4c illustrates one embodiment of a fixed diameter band 14. Band 14 is fabricated from a silicone tube (ID 2-3 mm, OD 3-4 mm) or cast to shape ring like device with tube like handle and full or partial internal tract with a Shore value of 5-40. The silicon component is reinforced via nylon, metallic wires or any other non-compliant material in order to prevent stretching of band 14 and enlargement of its ID. Wire 41 is looped through an over-molded lock 36 with ends 40 and 42 extending out of handle 38. Once band 14 is located around the hollow organ, ends 40 and 42 are tied to encircle the band. To release and remove band 14, ends 40 and 42 are cut or untied and the linearized band 14 is pulled out via handle 38.

Figure 4D:
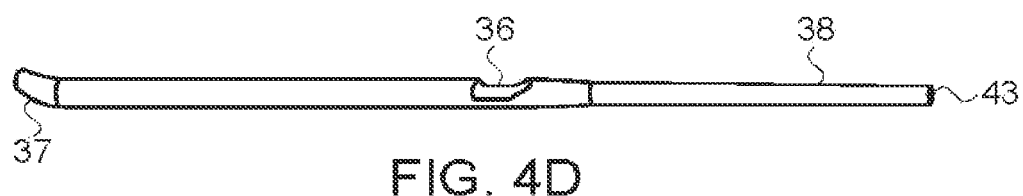
FIGS. 4D-E are perspective views of another embodiment of the band component of the present system shown in open (FIG. 4D) and closed (FIG. 4E) configurations.
Figure 4E:
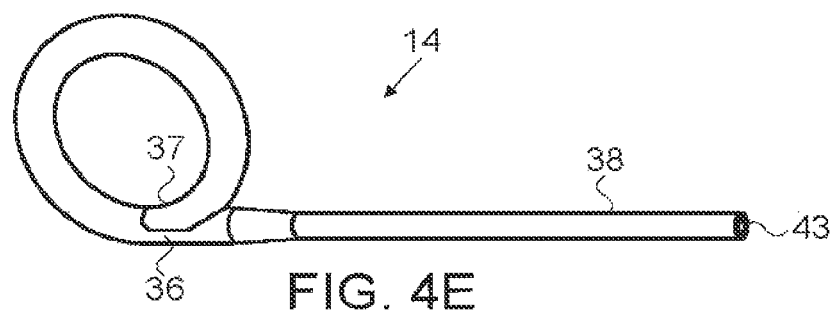

FIGS. 4d-e illustrate another embodiment of band 14 which includes a lock 36 configured for locking with a distal end 37 of band 14.

Distal end 37 and lock 36 are preferably molded from a rigid polymer which is overmolded with soft (e.g. Shore A of 20-50) silicone which forms the rest of band 14. Thus, the preferred configuration of this embodiment of band 14 includes rigid lock 36 and distal end 37 partially covered (internal surface and sides of band 14) by silicone. This enables lock 36 and end 37 to accurately mate and lock, while ensuring that the hollow organ is only exposed to the soft silicone portion of band 14.

Band 14 includes an internal wire (not shown) running a length of lumen 43 from handle 38 to distal end 37. Pulling of this wire from handle 38 circularizes band 14 and mates and locks distal end 37 with lock 36, thus transforming it from the linear configuration shown in FIG. 4d to the circular configuration shown in FIG. 4e.

Locking can be achieved by aligning a hole in distal end 36 with a hole in lock 36. Running a wire from handle 38 into and out of these holes can be used to secure/release distal end 37 to/from lock 36 (respectively).

Alternatively, band 14 can be circularized and locked manually via a flexible tooth (in lock 36) which engages a slit formed in distal end 37. A locking wire positioned at handle 38 can be connected to the flexible tooth and when pulled the wire flexes the tooth out of the slit and distal end 37 is released and disconnected from lock 36. It will be appreciated that band 14 can be preformed in the circular configuration shown in FIG. 4e, in which case pulling on the internal wire would linearize band 14 to the configuration shown in FIG. 4d.

Figure 6A:
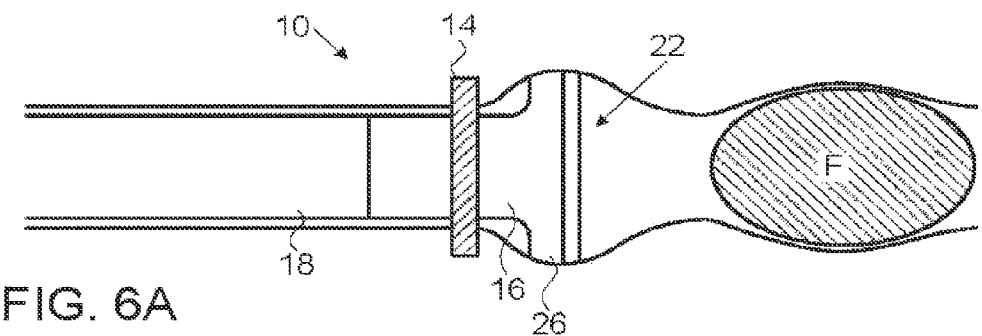
FIGS. 6A-C illustrate movement of fecal material through the present system when utilized as a bypass in a colon.
Figure 6B:
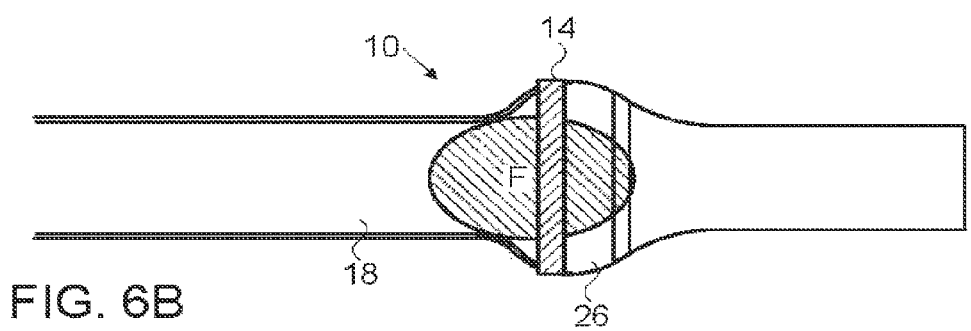
Figure 6C:
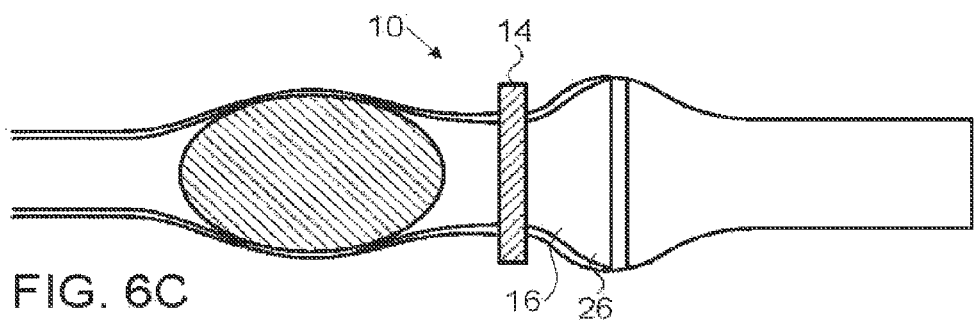

FIGS. 6a-c illustrate movement of feces through system 10 when positioned in a colon. A peristaltic wave forces fecal material (F) into opening 22 (FIG. 6a) of sleeve 12 thereby pushing sleeve 12 downstream and radially expanding it and the colon. Sleeve 12 migrates downstream until balloon 26 of sleeve 12 is stopped at the region of band 14 (FIG. 6b). The fecal material migrates passed the region of band 14 and the back wave of peristalsis pushes sleeve 12 back upstream.

Sleeve 12 is preferably delivered by a dedicated delivery apparatus which is referred to herein as apparatus 50.

As shown in FIGS. 5a-c, apparatus 50 includes an external tube 52 (which can be fabricated from PTFE or any other low friction material) fitted with a hollow nosecone 54 on its distal end. An internal tube 56 (can be fabricated from nylon or a Polyether block amide such as Pebax) is fitted within external tube 52 and a constraining compliant tube 58 (can be fabricated from nylon, polyurethane, latex or other) is connected to the distal end of internal tube 56. A tubular net structure 60 is connected to internal tube 56 proximally to constraining compliant tube 58.

Tubular sleeve 12 is folded around external tube 52 and is covered by tubular net structure 60. Both tubular sleeve 12 and tubular net structure 60 which covers it are constrained by tube 58. A first handle 62 connected to the proximal side of external tube 52 and a second handle 64 is connected to the proximal end of internal tube 56.

Delivery of tubular sleeve 12 into the hollow organ is effected as follows: Handle 62 is held in place while handle 64 is pulled out to push out—around nose cone 54 (in a distal direction)—both tubular net structure 60 and constraining compliant tube 58. This will release tubular sleeve 12 into the distal end of external tube 52 and allow device 10 expansion thereof. Tubular net structure 60 acts to reduce and normalize the friction between tubular sleeve 12 and tube 58 allowing for controlled, easy release.

The present system can be used in any anastomosis procedure which requires leakage protection. An Example of one commonly performed anastomosis procedure is provided below.

Figure 7:
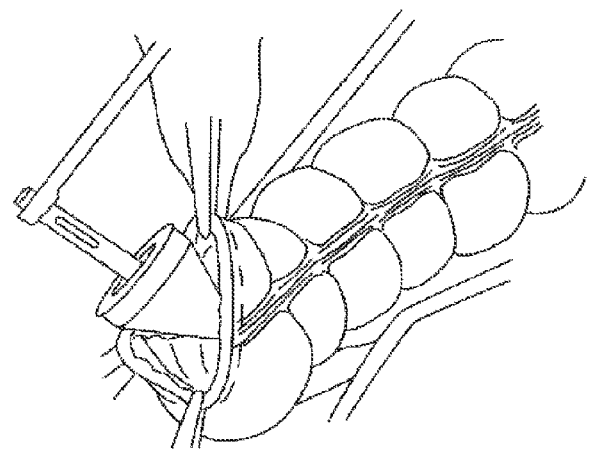
FIGS. 7-8 illustrate a standard anastomosis procedure on a resected colon.
Figure 8:
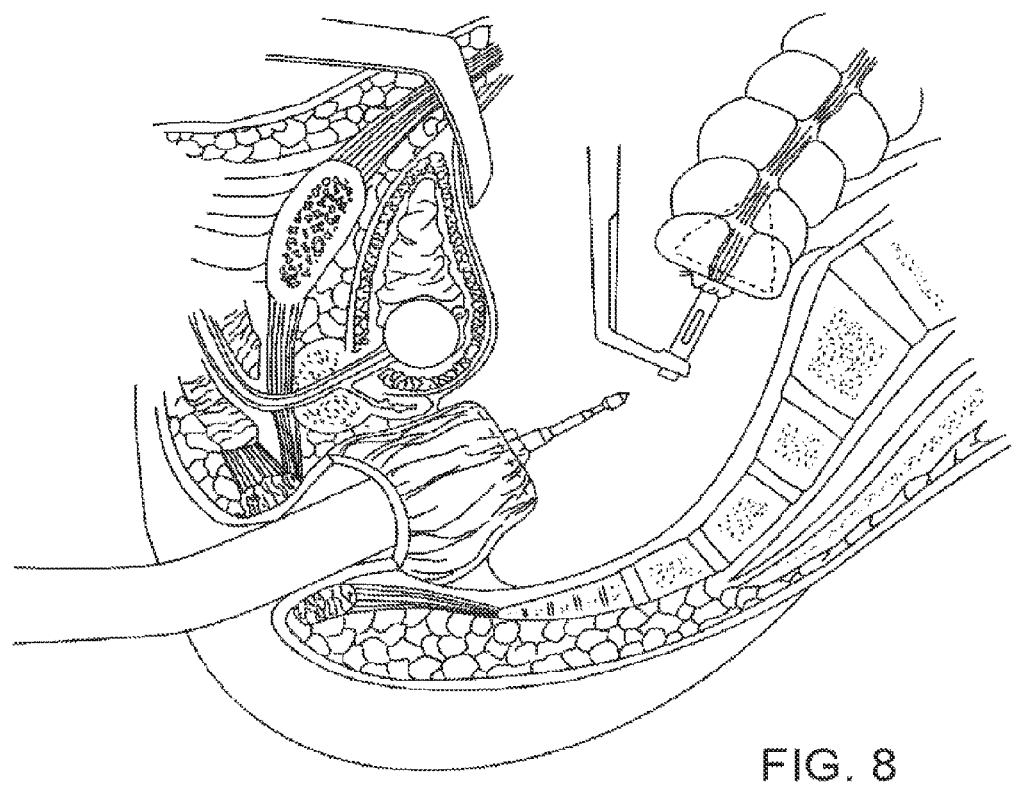
Figure 9:
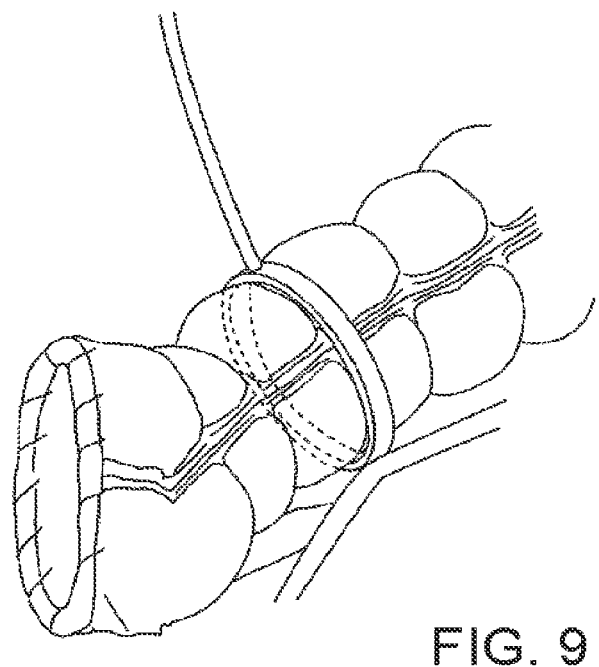
FIGS. 9-13 illustrate use of one embodiment of the present system in a anastomosis procedure on a resected colon.
Figure 10:
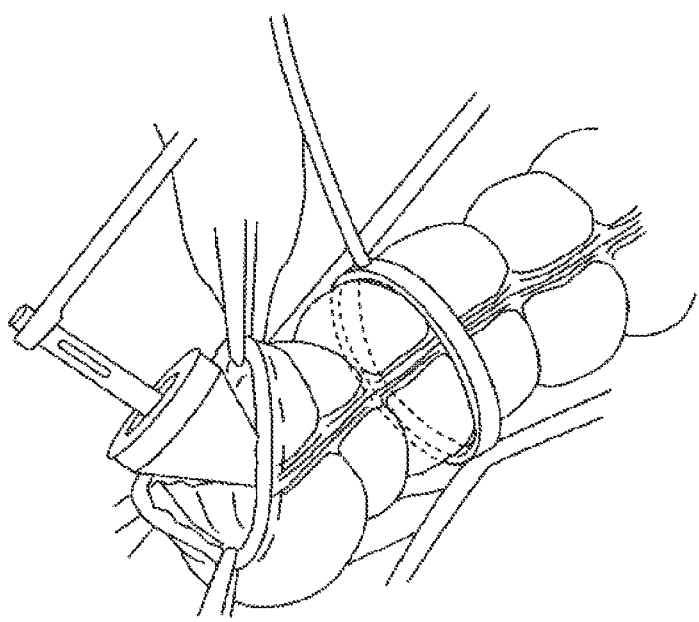
Figure 11:
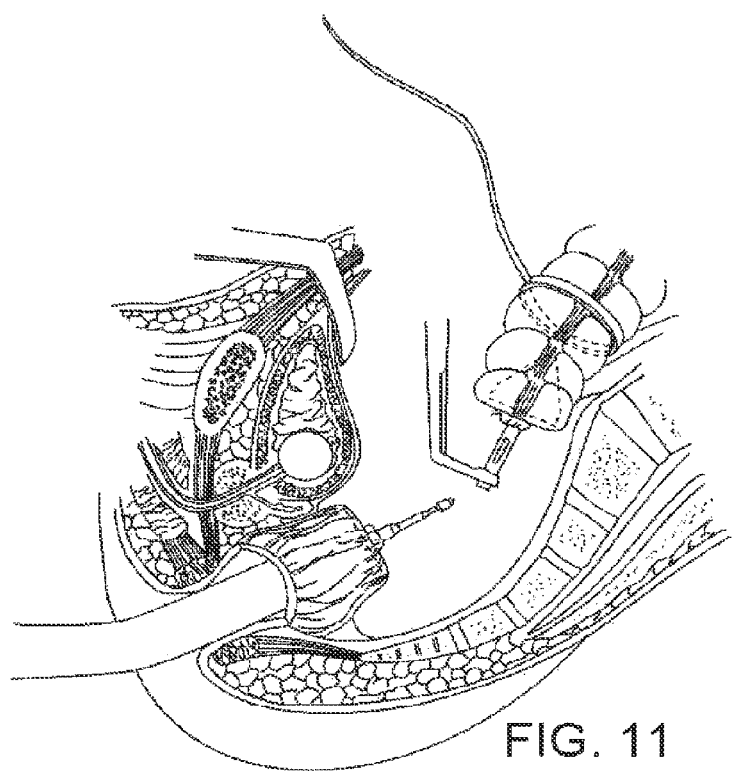
Figure 12:
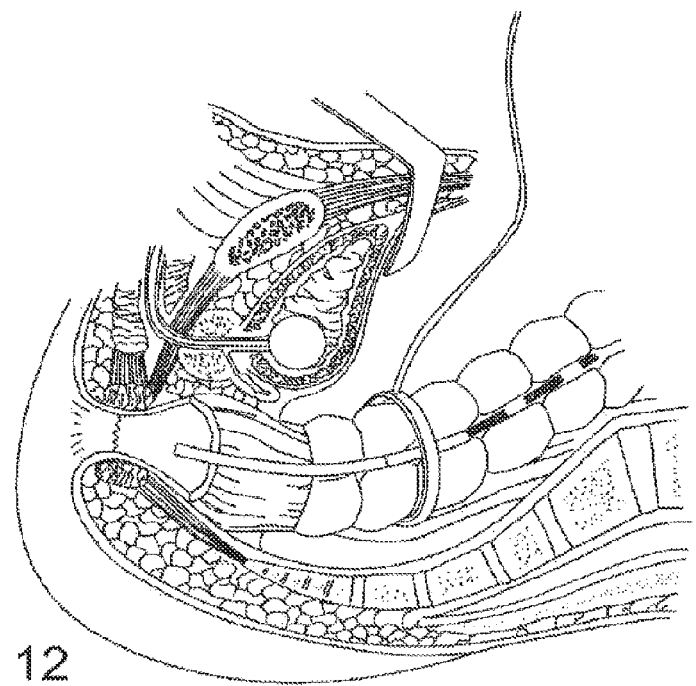
Figure 13:
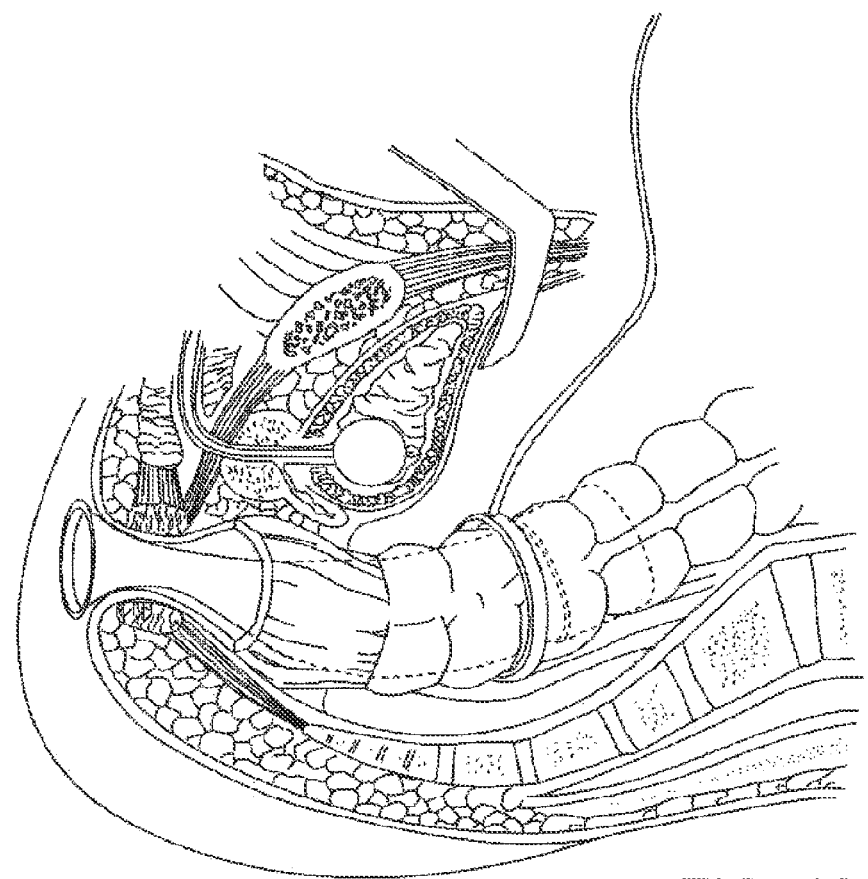
Figure 14:
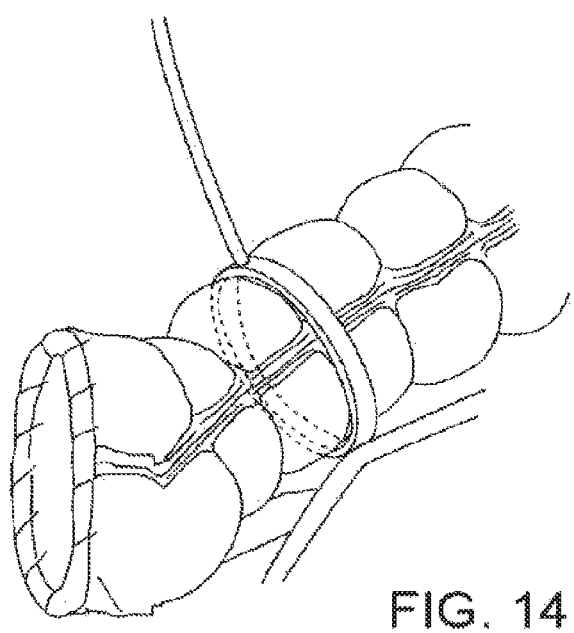
FIGS. 14-18 illustrate use of another embodiment of the present system in a anastomosis procedure on a resected colon.
Figure 15:
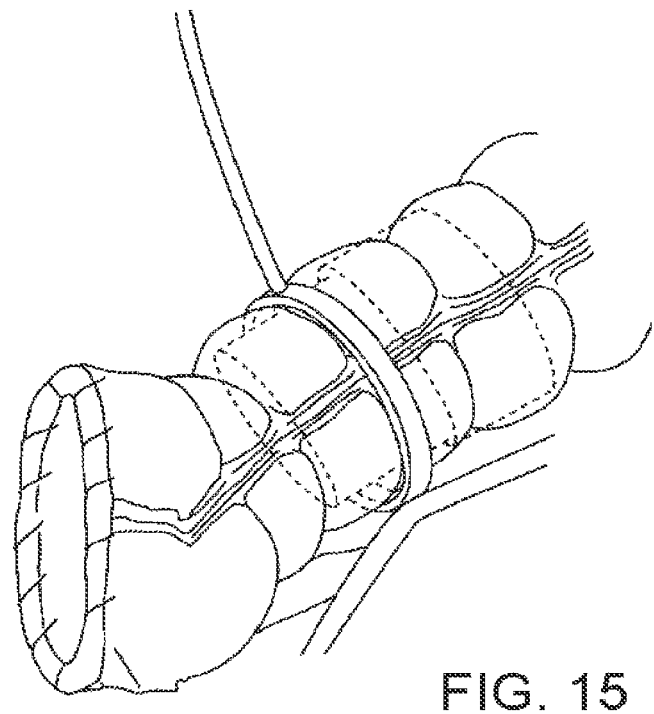
Figure 16:
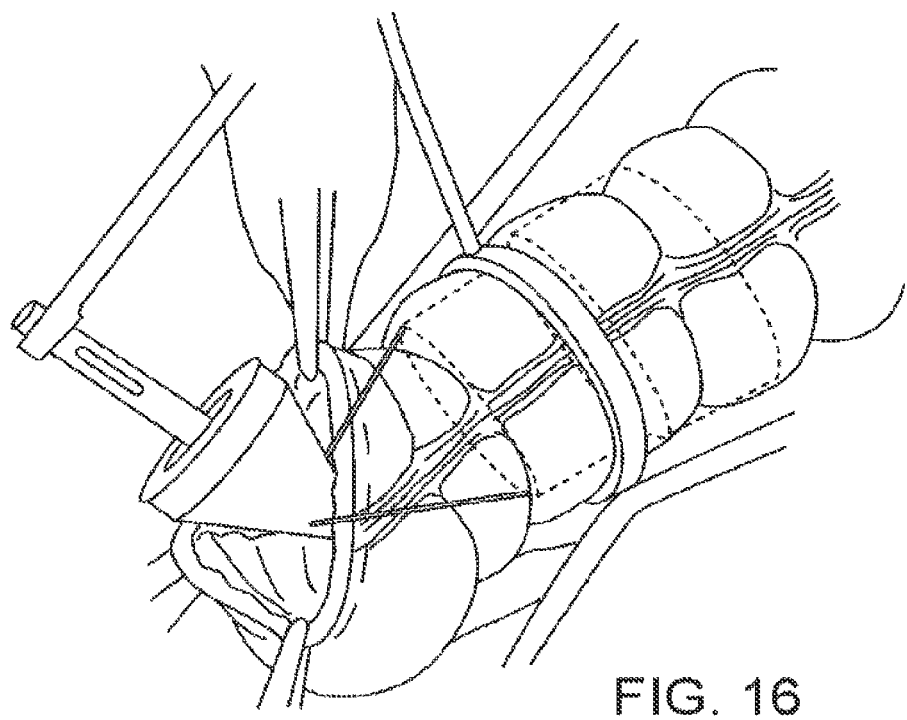
Figure 17:
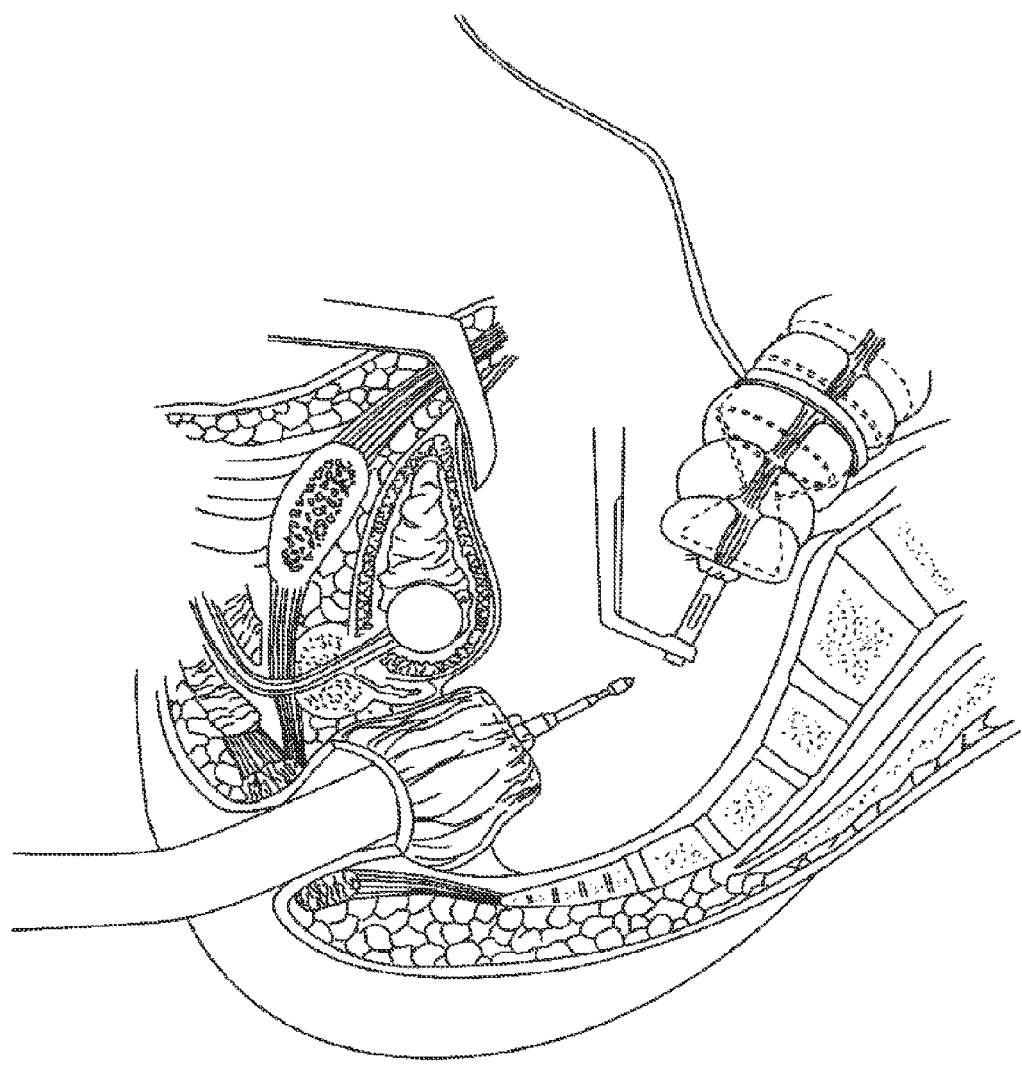
Figure 18:
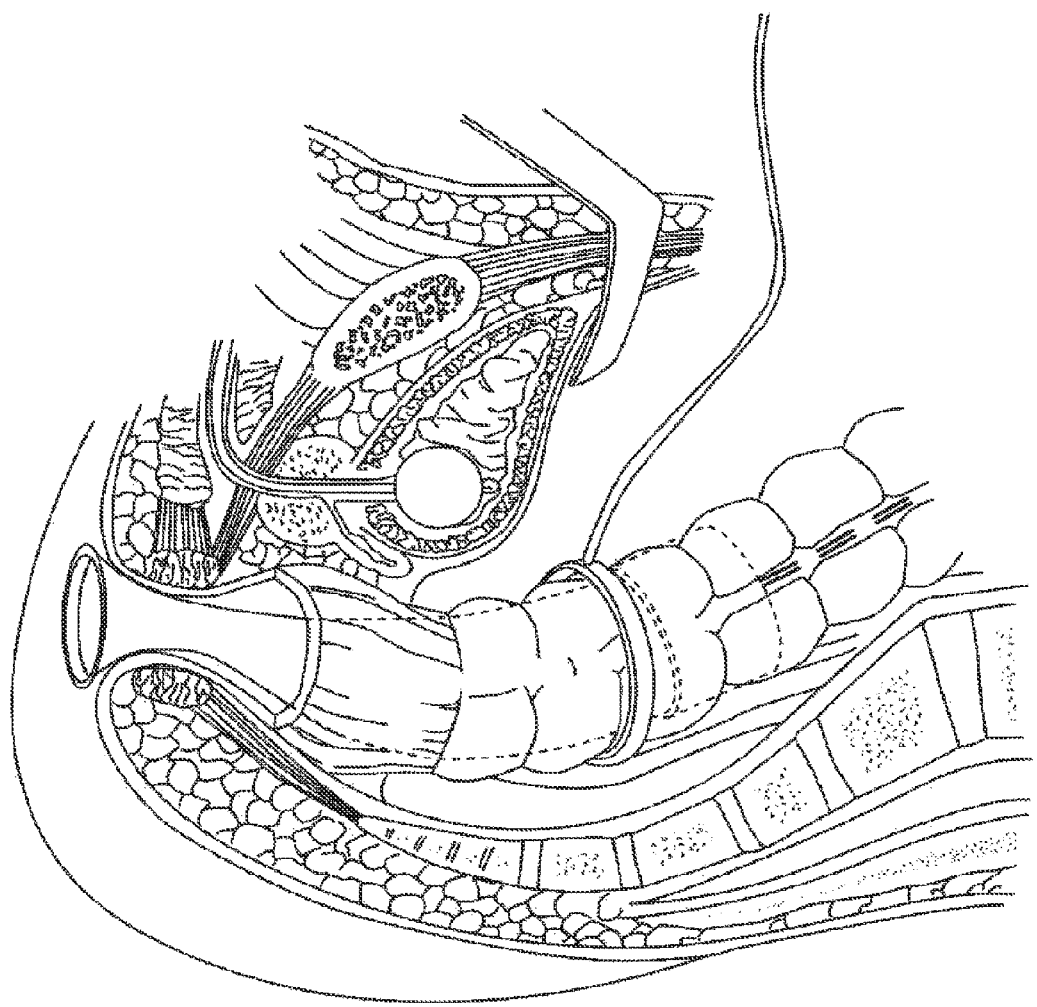

In a standard colorectal anastomosis procedure (shown in FIGS. 7-8) a section of the colon is resected and prepared for reconnection. A stapler anvil is inserted into the proximal section of the colon and the stapler is inserted through the anal orifice and advanced into the distal stump of the colon, the stapler is then connected to the anvil. The stapler is fired to create the anastomosis and then removed through the anal orifice. A catheter is advanced through the anal orifice and used to inflate the anastomosed colon with air, gas or a saline solution in order to check for leaks at the anastomosis site. One or more drainage tubes are routed from the anastomosis site through the abdominal wall and positioned outside the body. The drains are employed for 5-7 days depending on the drained content and patient condition. In the case of anastomosis site leakage, the drain can be employed for 14-21 days.

The system of the present invention is employed along the standard procedure using one of several approaches. The following describes two preferred approaches.

In the procedure shown in FIGS. 9-13, a band delivered as a linear strip through an abdominal incision is fitted around the colon 4-10 cm above the proposed anastomosis site (i.e. 4-10 cm proximal to the proposed site) with its deployment mechanism (handle) extending outside the body. In open surgery the handle connected to the external band will be hanging out or folded into a compact configuration such that it will not interfere with the anastomosis process. Alternatively, the handle can be connected to the external band following anastomosis and deployment of the sleeve. In minimal invasive procedure the handle will be pushed into the abdominal cavity with the proximal part of the colon. The stapler anvil is inserted into the proximal section of the colon and the stapler is inserted through the anal orifice and advanced into the distal stump of the colon, the stapler is then connected to the anvil. The stapler is fired to create the anastomosis and then removed through the anal orifice. A catheter is advanced through the anal orifice and used to inflate the anastomosed colon with air, gas or a saline solution in order to check for leaks at the anastomosis site. A delivery catheter carrying a tubular sleeve is then inserted through the anal orifice and positioned with its distal end above the anastomosis site and distally (above) the band. The tubular sleeve is deployed by inflating the cuff via injection of saline or air through the fluid conduit port. The proximal end of the tubular sleeve which resides outside the anal orifice is then pulled and cut to size. One or more drainage tubes are routed from the anastomosis site through the abdominal wall and positioned outside the body. The drainage tubes and band are removed following healing of the anastomosis site.

In the procedure shown in FIGS. 14-18, both the band and the tubular sleeve are positioned prior to anastomosis and the cuff is inflated via injection of saline or air through the fluid conduit port. The distal part of the folded sheath is attached to the anvil part of the stapler with stickers or glue or sutures. The 2 sections of the colon are then anastomosed once the stapler is fired and opened and pulled out of the anus it will pull out the sheath outside the anus. In this method once the sheath is fully deployed the surgeon can perform an air leak test using a common approach or by using the lumen in the sleeve for injecting a contrast material to the anastomosis site. Alternatively the anvil can be used to pull out sutures which can then be used to pull out the sleeve. In this approach an air leak test could be performed following pulling of the sutures and prior to pulling of the sleeve. The proximal end of the tubular sleeve which resides outside the anal orifice is then pulled and cut to size. One or more drainage tubes are routed from the anastomosis site through the abdominal wall and positioned outside the body. The drainage tubes and band are later removed.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

The present inventors utilized silicone tubing in order to assess the anchoring and sealing capabilities of an internal bypass sleeve held in position by an external band. The internal sleeve was fabricated from a silicone tube 200 mm length, 28 mm diameter and a thickness of 0.6 mm. The tube was attached to an internal ring made of a 2 mm diameter stainless still spring. Fresh porcine colon, 500 mm in length from the anus was used as the testing bed as described below. An external ring was fabricated from a silicon tube and was fitted with a dedicated connector.

Figure 19:
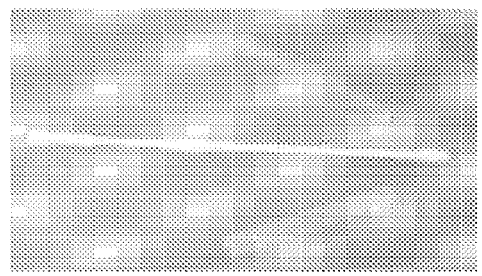
FIG. 19 illustrates one configuration of an early prototype of a delivery apparatus.
Figure 20:
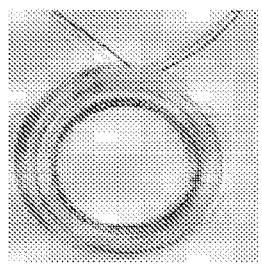
FIG. 20 illustrates one configuration of an early prototype of an external band shown with respect to the internal ring portion of the internal sleeve.
Figure 21A:
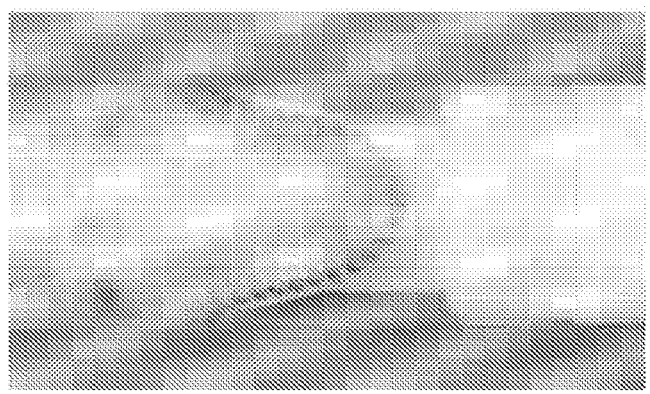
FIGS. 21A-D illustrate deployment of an internal sleeve mounted on a delivery apparatus.
Figure 21B:
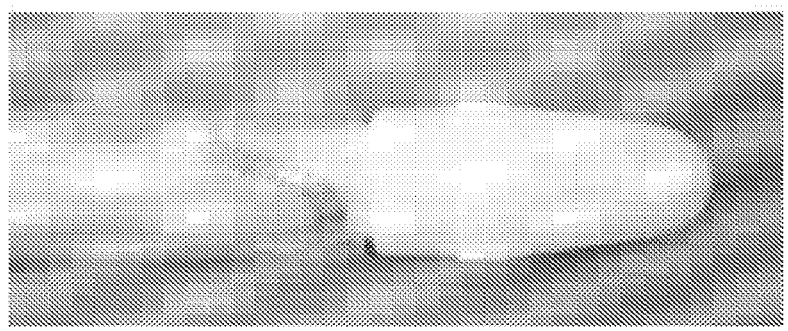
Figure 21C:
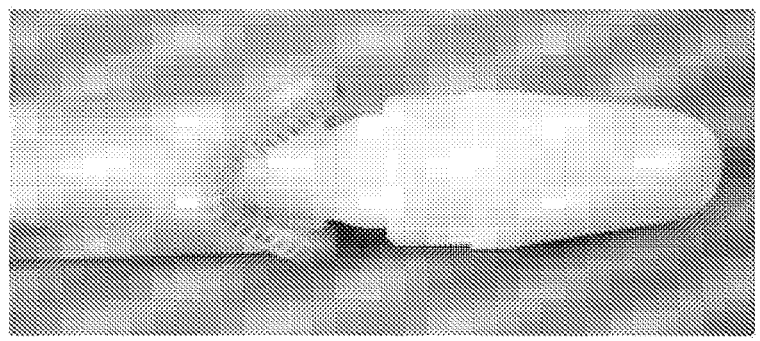
Figure 21D:

The delivery system for the internal sheath is shown in FIG. 19 and the external band is shown in FIG. 20. The sleeve and ring are loaded into the delivery tube (FIG. 21A) which is pulled back to expose the internal ring (FIGS. 21b-c) and attached sleeve (FIG. 21D) thereby deploying the sleeve.

Anchoring Force

The external band was closed around the porcine colon and the sleeve and internal ring were delivered and deployed using the delivery tube, the external band was then tightened around the colon to secure the sleeve in position. The sleeve was pulled manually from the anus end to check fixation via the external ring.

Sealing

Sealing was checked on the flow test apparatus by mounting the porcine colon with anchored bypass sleeve between inflow and outflow tubing. Water flowing through the colon bypassed completely through the internal sleeve without contacting the colon wall.

Example 2

Figure 22:
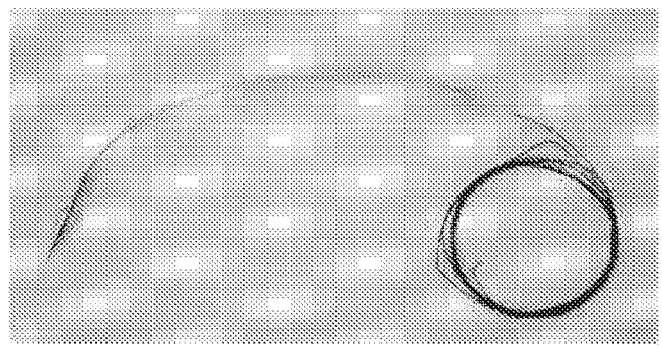
FIG. 22 illustrates the components of one external band prototype prior to assembly of the band.

A similar system to the one described in example 1 was deployed in test animals (Pigs) for 14 days in order to evaluate its anchoring and sealing capabilities in-vivo. The external ring had a minor change, adding a metal introducer to allow easier insertion through the colon mesentery tissue (FIG. 22).

Figure 24:
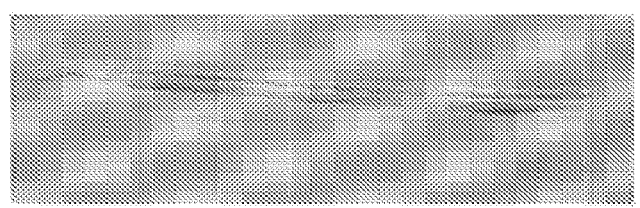
FIG. 24 illustrates the components of another external band prototype prior to assembly of the band.

The system used included a sleeve 200 mm in length and 30 mm in diameter with a thickness of 0.4 mm. The sleeve was glued at its distal end around a 0.2 mm metal wire shaped as a ring. The external ring was fabricated from a 4 mm diameter silicon tube connected end-to-end into a ring shape via a prolene suture which was threaded inside the tube (FIG. 24) and tied to close the tube into a band.

Delivery was effected using a dedicated delivery apparatus which was similar in design to that shown in Example 1.

Surgical Procedure

Cefalysin (7 mg/kg, IM, q 24 hr) was administered i.m. to the pig 48 hours prior to surgery to reduce bowel bacterial load and thus reduce probability of post-operative wound infections. Cefalysin IM (7 mg/kg, IM, q 24 hr) and Metronidazole (500 mg/pig I.V. daily for 3 days) were administered an hour prior to the surgery. The colon was prepared with a laxative and enema.

The abdominal skin was shaved in the area where the midline incision was planned and the operation was performed via midline incision.

The colon was mildly mobilized with preservation of the mesentery and its blood supply. The external band was introduced through a small channel created in the mesentery tissue using a metal introducer. The metal introducer was then pulled out and the suture end of the band was used to close the band around the colon approximately 20 cm from the anus.

The band closing procedure was more difficult than expected. The connector tube that was glued to one side of the band was disconnected and it took the surgeon approximately 5 minutes to close the band properly and tie the suture ends. The band was closed to a diameter which applied no appreciable pressure on the colon wall.

The delivery apparatus was introduced through the anus making sure that the distal tip of the delivery system is proximal to the external band. The internal ring (mounted on the sleeve) was opened and its position was verified (distal to the external band). The delivery apparatus was pulled out and the internal sleeve deployed. Deployment of the sleeve was difficult due to vacuum created by the colon tissue around the silicon sleeve. Final deployment of the sleeve was achieved only with disassembly of the delivery system. Testing of the positioned system revealed that the outer band could not prevent migration of the sleeve since the internal ring rotated vertically and thus it slipped through the external ring. A different sleeve with a shore A 40 ring was deployed but the problem of ring sliding reoccurred. The external band was left in position and anchored with a Vicryl 3/0 suture into the serosa. The abdominal cavity was closed using a conventional approach. The animal was monitored for 21 days until a new sheath configuration was fabricated.

Example 3

Figure 23:
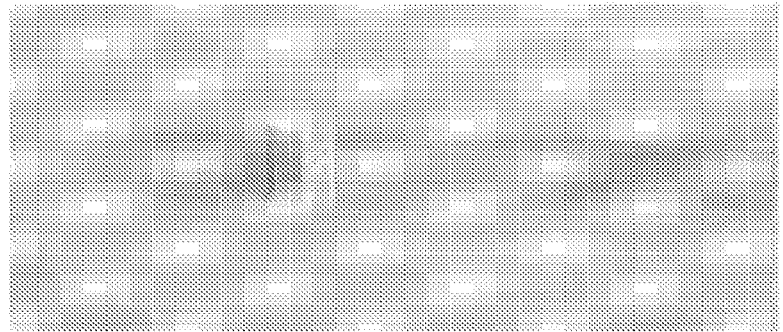
FIG. 23 illustrates one configuration of an early prototype of an internal sleeve fitted with a crown.

A system similar to that described in Example 3 but with a silicone "crown" (FIG. 23) surrounding an internal ring was fabricated and tested in animals. The crown was used in order to provide stability to the ring and prevent sliding of the sleeve through the external band. The external band was also modified and was made out of a standard 10 mm flat silicon drain that was tied with prolene 2/0 sutures (FIG. 23). The system was delivered as described in Example 2.

Results

The new sleeve design was easily inserted into the colon of a second test pig.

The external band was also easily deployed although it was difficult to accurately gauge the ID of the external band once in position. The operation lasted 20 minutes but the animal expelled the internal sleeve at day 4 post-op with its first bowel emptying.

This experiment showed that the internal ring needs to be redesigned to allow a significant gap between its diameter and the external ring diameter and that closure of the external band should be modified to allow for accurate closing at a set diameter.

The test animal was kept for a future operation following redesign of the internal sleeve and band.

Example 4

Figure 25:
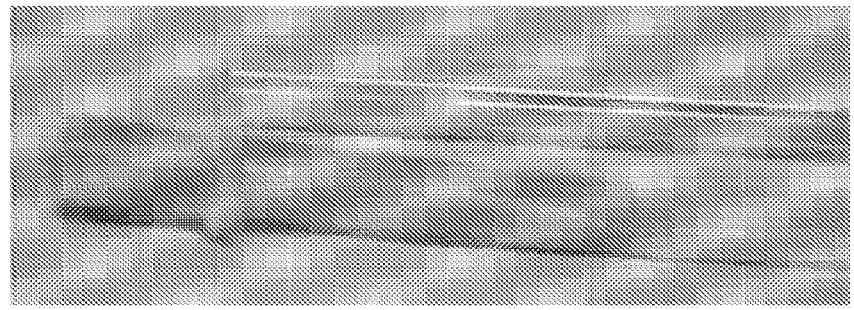
FIG. 25 illustrates another configuration of an early prototype of an internal sleeve fitted with a crown.

A new external band design and a new delivery tube and sleeve were tested in 2 animals. The prototype system included a 0.4 mm silicon sleeve 300 mm in length and 30 mm in diameter (FIG. 25). The sleeve was wrapped and glued at its proximal end around a 0.2 mm silicon ring. Proximal to the ring there is a thicker silicone "crown" which should provide stability to the ring and prevent migration through the external band. The external band (FIG. 24) was fabricated from a 7 mm flat silicon drain with a special plastic connector. An internal prolene suture was threaded inside the flat drain and was used to tie and close the external band. The delivery system was fabricated from plastic.

Results

Figure 26:
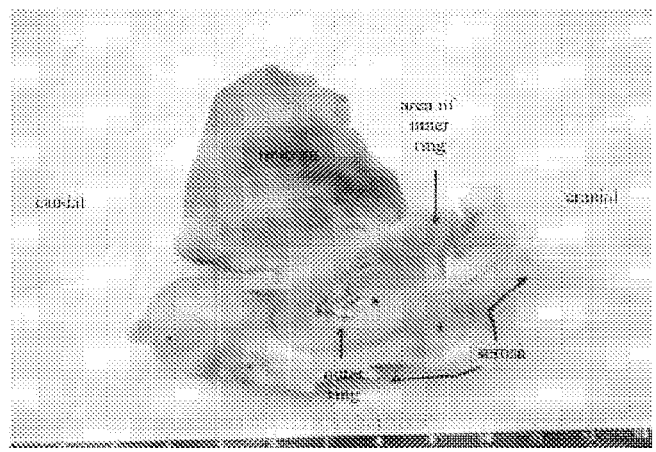
FIG. 26 illustrates a tissue sample obtained from a pig colon fitted with an early prototype of the present system for 14 days.

The new system was tested in two animals (pigs) using the methodology described above. In the first test animal, the system stayed in place for 14 days, following which the animal was scarified. A colon sample obtained from the test animal showed signs of colon wall damage (FIG. 26). The sample was analyzed at a pathology lab which concluded that there was extensive necrosis and fibrosis of the tunica muscularis, which is expanded by large areas of necrotic debris, mixed with numerous neutrophils and bacteria. The area is surrounded by neutrophils and reactive fibrous tissue (abscess). The lesions involve the tunica muscularis and submucosa. There is no evidence of involvement of muscularis mucosa or lamina propria. Crypts in colorectal mucosa are within normal ranges. There is mild proprial interstitial infiltration with neutrophils, fewer macrophages and lymphocytes. Most of the mucosal epithelium is not resent, but the change is artefactual, likely due to handling and orientation of the tissue.

In the second test animal the system remained in position for 14 days following which the animal was scarified. Over the 14 days, the system moved back and forth within the colon (the sleeve moved 4-5 cm out and into the anus).

Figure 27:
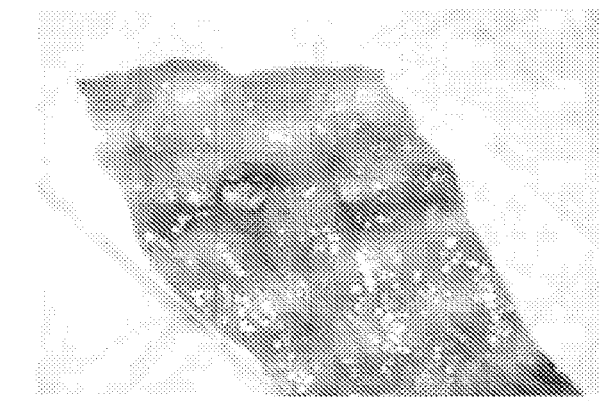
FIG. 27 is a colon wall tissue sample showing erosion of the colon wall caused by the deployment mechanism of an early prototype the external band.

A colon sample obtained from the animal showed evidence of two penetration points in the colon mucosa. (FIG. 27). Close examination of the penetration points revealed that they are in location where the band deployment tube (handle) connects to the band.

Following this experiment, the present inventors concluded that the diameter of the external band was too small and probably created pressure on the colon wall. As such, it was decided that the external band be re-designed to allow more freedom over the colon and that the locking mechanism be changed to allow no contact with the colon wall.

In addition, the internal ring of the sleeve must be redesigned to keep the same proportions between the internal (sleeve) and external (band) diameters in order for the band to function as a migration stop.

Example 5

Tissue erosion caused by the external band as well as sleeve migration against the external band, has led the present inventor to redesign the external band and internal sleeve.

Figure 28:
FIG. 28 illustrates one prototype of the present system.
Figure 29:
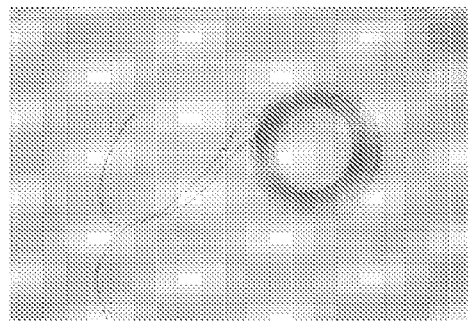
FIG. 29 illustrates a prototype of an external band.

The redesigned system included a 0.2 mm silicon Shore A 20 sheath 400 mm in length and 25 mm in diameter (FIG. 28). The sleeve was wrapped and glued at its distal end around a 10 mm 20 shore silicon O ring. Proximal to the ring there is a thicker silicone "crown" which should provide stability to the ring and prevent sliding through the external band. The external band was fabricated from an O-ring with a diameter of 32 mm which was fitted with an outer silicone tube threaded with a nylon suture and fitted with a metal connector (FIG. 29). The delivery system was made of plastic.

The modified band and sleeve were delivered and positioned in a pig using the procedure described above.

Results

Figure 30:
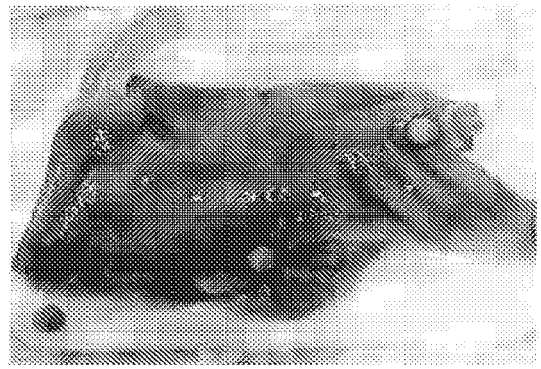
FIG. 30-32 are samples of resected colon wall tissue obtained from a test animal fitted with an advanced prototype of the present system.
Figure 31:
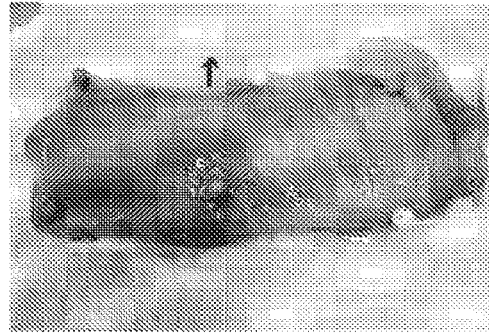
Figure 32:

The system remained in the test animal for 14 days, following which the pig was sacrificed and the colon resected. Three samples were collected from the resected colon (FIGS. 30-32). The colon samples revealed no wall damage.

These results revealed that the diameters of both the internal ring and the external band of this system prototype provide stable fixation without leading to tissue erosion at the colon wall.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Example 6

Two and Three Balloon Sleeve

The sleeve described in Example 5 was modified to enhance device delivery, sealing and prevent angulation of the upper portion of the tubular sleeve with respect to the longitudinal axis of the colon (yaw). The modified prototypes were tested in pigs as described above.

Figure 33:
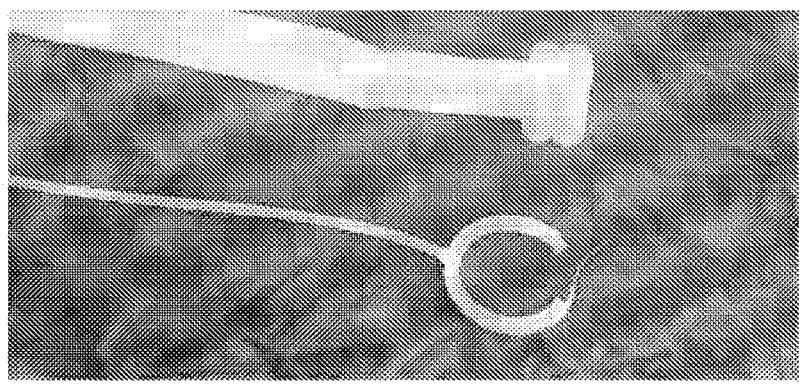
FIG. 33 illustrates a prototype of the present system which includes a sleeve having two closely spaced balloons.

A two balloons system (FIG. 33) was fabricated as described in Example 5 with two closely spaced balloons (45 mm apart) having an outer diameter (OD) of 55 mm when inflated; the dimensions of the sleeve were as described in Example 5.

The results with this two balloon configuration were not satisfactory since the sleeve rotated (yaw) inside the colon causing colon obstruction and in one case, expulsion of the sleeve. It was concluded that in order to enhance stability, the distance between the balloons should be close to 2 times the OD of the balloons.

Figure 34:
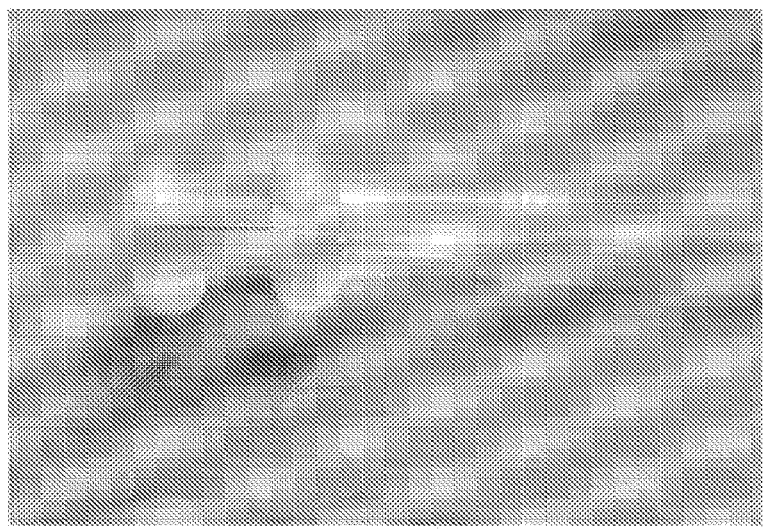
FIG. 34 illustrates a prototype of the sleeve which includes two spaced apart balloons.
Figure 35:
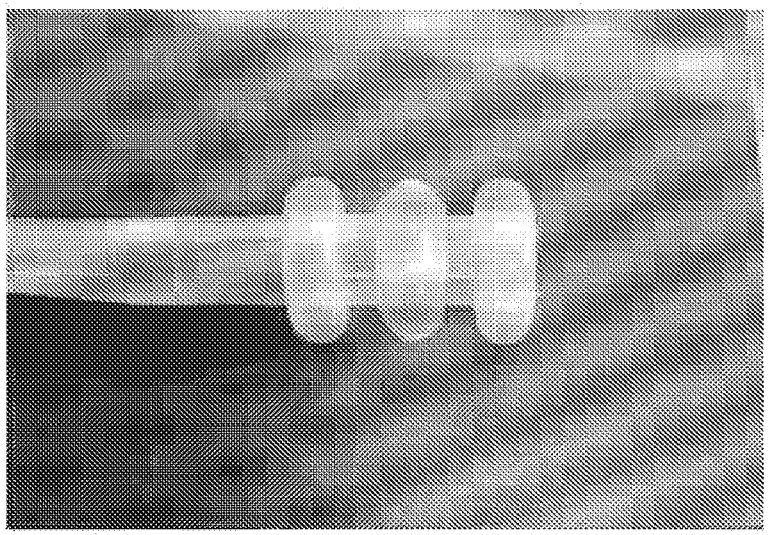
FIG. 35 illustrates a prototype of the sleeve which includes three balloons.

Two types of solutions were tested for rotational stability: a sleeve having two balloons spaced apart by 45 mm (FIG. 34), this configuration was also tested with or without metal struts between the balloons (struts shown in FIG. 34); and a sleeve having three balloons spanning a 50 mm region (FIG. 35).

The results with both configurations demonstrated enhanced stability with no rotations or expulsions of the sleeve.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for bypassing an anastomosis site in a colon, the system comprising:
    a band, configured for positioning around an external surface region of the colon;
    a tubular sleeve having a portion configured for spanning the anastomosis site at an internal surface of the colon, the tubular sleeve including a first tubular region extending to a contiguous second tubular region, the first tubular region including an inflatable structure having:
    an outer diameter that, when inflated, is greater than an outer diameter of the contiguous second tubular region;
    a first, proximal-most portion that, when inflated, is configured to cooperate with the band to limit movement of the tubular sleeve in a downstream direction of the colon while enabling migration of the tubular sleeve in an upstream direction of the colon;
    a second portion distal to the first proximal-most portion, the second portion being configured to stabilize the tubular sleeve within the colon; and
    a distance from a proximal edge of the first, proximal-most portion to a distal edge of the second portion that, when the inflatable structure is inflated, is greater than the outer diameter of the first tubular region and less than or equal to twice said outer diameter of the first tubular region.

2. The system of claim 1, wherein the inflatable structure includes at least a first, proximal balloon, constituting the first, proximal-most portion and a second, distal balloon constituting the second portion.

3. The system of claim 1, wherein an internal diameter of the band is equal to, or greater than, an external diameter of the colon and less than the outer diameter of the inflatable structure of the first tubular region.

4. The system of claim 1, wherein the band is configured to extend through an abdominal wall when the band is positioned around the external surface region of the colon.

5. The system of claim 1, wherein the first tubular region is more rigid than the second tubular region.

6. The system of claim 5, wherein the first tubular region includes elements for increasing a longitudinal rigidity thereof.

7. The system of claim 6, wherein the elements are longitudinal struts.

8. The system of claim 1, wherein the tubular sleeve includes a fluid conduit for dispensing a fluid into the colon.

9. The system of claim 1, wherein an internal surface of the band is fabricated from a polymer having a Shore A value of between approximately 40 and 60.

10. The system of claim 1, wherein the band is fabricated from a biodegradable material.

11. The system of claim 1, wherein the second portion is configured to inhibit yaw of the first tubular region when the inflatable structure is inflated.

12. The system of claim 1, wherein the band is configured for anchoring to the external surface region of the colon.

13. The system of claim 12, wherein the band is configured for anchoring to a serosa or a mesentery of the colon.

14. A method of internally shielding an anastomosis site in a colon of a subject, the method comprising:
    positioning within the colon a tubular sleeve having a first tubular region extending to a contiguous second tubular region, the first tubular region including an inflatable structure having an outer diameter that, when inflated, is greater than an outer diameter of the contiguous second tubular region, wherein the inflatable structure includes a first, proximal-most portion that, when inflated, is configured to cooperate with a band to limit movement of the tubular sleeve in a downstream direction of the colon while enabling migration of the tubular sleeve in an upstream direction of the colon, wherein a second portion of the inflatable structure, distal to the proximal-most portion of the inflatable structure, when inflated, is configured to stabilize the tubular sleeve within the colon, and wherein a distance from a proximal edge of the first, proximal-most portion to a distal edge of the second portion, when inflated, is greater than the outer diameter of the first tubular region and less than or equal to twice said outer diameter of the first tubular region;
    positioning the band around an external surface region of the colon upstream of the anastomosis site and downstream of the inflatable structure; and
    inflating the inflatable structure thereby restricting downstream migration of the tubular sleeve and shielding the anastomosis site in the colon.

15. The method of claim 14, wherein the inflatable structure includes at least a first, proximal-most balloon, which, when inflated, is configured to cooperate with the band to limit movement of the tubular sleeve in a downstream direction of the colon while enabling migration of the tubular sleeve in an upstream direction of the colon, and at least a second balloon, which, when inflated, is configured to stabilize the tubular sleeve within the colon.

16. The method of claim 14, wherein positioning the tubular sleeve includes delivering the tubular sleeve through an anal orifice.

17. The method of claim 14, wherein positioning the band includes forming a portion of a linear strip into a loop around the external surface region of the colon.

18. The method of claim 14, further comprising delivering the band through an abdominal wall of the subject.

19. The method of claim 17, wherein following positioning of the band, a portion of the linear strip extends through an abdominal wall.

20. The method of claim 14, wherein positioning the tubular sleeve includes inflating the inflatable structure within the colon.

21. The method of claim 20, wherein the tubular sleeve further includes at least one inflation conduit and inflating the inflatable structure includes delivering fluid from an inflation port positioned outside a body of the subject to the inflation conduit.

22. The method of claim 21, wherein the fluid delivered from the inflation port to the inflation conduit is a liquid.

23. The method of claim 21, wherein the fluid delivered from the inflation port to the inflation conduit is a gas.

24. The method of claim 14, wherein the band is anchored to a serosa or a mesentery of the colon.

* * * * *